(12) United States Patent
Ilekti et al.

(10) Patent No.: US 8,945,524 B2
(45) Date of Patent: Feb. 3, 2015

(54) COSMETIC HEAT TREATMENT METHOD

(75) Inventors: Philippe Ilekti, Maison-Alfort (FR); Xavier Blin, Paris (FR); Beatrice Toumi, Verrieres le Buisson (FR)

(73) Assignee: L'Oreal, Paris (FR)

( * ) Notice: Subject to any disclaimer, the term of this patent is extended or adjusted under 35 U.S.C. 154(b) by 694 days.

(21) Appl. No.: 13/054,681

(22) PCT Filed: Jul. 22, 2009

(86) PCT No.: PCT/FR2009/051477
§ 371 (c)(1),
(2), (4) Date: May 9, 2011

(87) PCT Pub. No.: WO2010/010304
PCT Pub. Date: Jan. 28, 2010

(65) Prior Publication Data
US 2011/0318082 A1   Dec. 29, 2011

Related U.S. Application Data

(60) Provisional application No. 61/096,393, filed on Sep. 12, 2008.

(30) Foreign Application Priority Data

Jul. 24, 2008   (FR) .................... 08 55085

(51) Int. Cl.
| | | |
|---|---|---|
| A61Q 1/06 | (2006.01) | |
| A61Q 1/04 | (2006.01) | |
| A45D 40/08 | (2006.01) | |
| A61K 8/81 | (2006.01) | |
| A45D 40/18 | (2006.01) | |
| A45D 40/20 | (2006.01) | |

(52) U.S. Cl.
CPC ........ *A61Q 1/06* (2013.01); *A45D 40/08* (2013.01); *A61K 8/8105* (2013.01); *A61K 8/8152* (2013.01); *A45D 40/18* (2013.01); *A45D 40/20* (2013.01); *A45D 2200/155* (2013.01); *A61K 2800/884* (2013.01)
USPC ............................................. 424/64; 424/401

(58) Field of Classification Search
None
See application file for complete search history.

(56) References Cited

U.S. PATENT DOCUMENTS

| | | |
|---|---|---|
| 2,676,182 A | 4/1954 | Daudt et al. |
| 3,627,851 A | 12/1971 | Brady |
| 3,772,247 A | 11/1973 | Flannigan |
| 4,935,484 A | 6/1990 | Wolfgruber et al. |
| 5,082,706 A | 1/1992 | Tangney |
| 5,110,890 A | 5/1992 | Butler |
| 5,156,911 A | 10/1992 | Stewart |
| 5,221,534 A | 6/1993 | DesLauriers et al. |
| 5,248,739 A | 9/1993 | Schmidt et al. |
| 5,302,685 A | 4/1994 | Tsumura et al. |
| 5,319,040 A | 6/1994 | Wengrovius et al. |
| 5,519,063 A | 5/1996 | Mondet et al. |
| 5,736,125 A | 4/1998 | Morawsky et al. |
| 5,783,657 A | 7/1998 | Pavlin et al. |
| 5,817,302 A | 10/1998 | Berthiaume et al. |
| 5,998,547 A | 12/1999 | Hohner |
| 6,180,123 B1 | 1/2001 | Mondet |
| 6,478,493 B1 | 11/2002 | Cepeda et al. |
| 6,949,504 B2 * | 9/2005 | Mondet et al. ............... 514/1 |
| 2002/0005562 A1 | 1/2002 | Kim et al. |
| 2003/0150875 A1 | 8/2003 | Belanger |
| 2004/0096258 A1 | 5/2004 | Kim |
| 2005/0031400 A1 * | 2/2005 | Marcotte et al. .......... 401/129 |
| 2005/0050328 A1 | 3/2005 | Mizrah |
| 2005/0276767 A1 * | 12/2005 | Blin et al. .................. 424/63 |
| 2005/0287105 A1 | 12/2005 | Blin et al. |
| 2006/0008441 A1 | 1/2006 | Kanji et al. |
| 2006/0191957 A1 | 8/2006 | Axinte et al. |
| 2006/0193801 A1 * | 8/2006 | Blin et al. .................. 424/63 |
| 2007/0031361 A1 | 2/2007 | Herrmann et al. |
| 2007/0053859 A1 | 3/2007 | Bui et al. |
| 2007/0286665 A1 | 12/2007 | Bouix et al. |
| 2008/0143214 A1 | 6/2008 | McNamara et al. |
| 2008/0152678 A1 | 6/2008 | Shah et al. |
| 2010/0316587 A1 | 12/2010 | Barba et al. |

FOREIGN PATENT DOCUMENTS

| | | |
|---|---|---|
| DE | 101 50 619 | 4/2003 |
| EP | 0 223 603 | 5/1987 |
| EP | 0 550 745 | 7/1993 |
| EP | 0 708 114 | 4/1996 |
| EP | 0 951 897 | 10/1999 |
| EP | 1 454 612 | 9/2004 |
| FR | 2 888 498 | 1/2007 |
| FR | 2 894 472 | 6/2007 |
| FR | 2 918 272 | 1/2009 |
| FR | 2 926 022 | 7/2009 |
| JP | 2007 269763 | 10/2007 |
| WO | 01 19333 | 3/2001 |
| WO | 2005 075542 | 8/2005 |
| WO | 2009 080955 | 7/2009 |
| WO | 2009 104133 | 8/2009 |

OTHER PUBLICATIONS

Anonymous: "Brillants a levres," Research Disclosure Journal, ISSN 0374-4353, vol. 526, No. 20, total 8 pages, (Jan. 25, 2008) XP 007137951 (with partial English translation).

(Continued)

*Primary Examiner* — Jyothsna Venkat
(74) *Attorney, Agent, or Firm* — Oblon, Spivak, McClelland, Maier & Neustadt, L.L.P.

(57) ABSTRACT

A method of makeup and/or non-therapeutic care for non-fibrous human keratin material, particularly the skin, the mucus membranes thereof, or the nails, including: bringing an outer surface of a piece of solid cosmetic composition, having a temperature-sensitive dynamic rub coefficient, into contact with, or near, a heating device, said dynamic rub coefficient, at 25° C., being greater than or equal to 0.5, preferably 0.6, so as to heat said piece in a localized manner with a view to essentially softening only said outer surface and lowering the dynamic rub coefficient thereof; and applying the outer surface of the thus-heated composition onto the area to be treated.

8 Claims, 3 Drawing Sheets

(56) References Cited

OTHER PUBLICATIONS

International Search Report issued Mar. 30, 2010 in PCT/FR09/051477 filed Jul. 22, 2009.
International Search Report issued Mar. 9, 2010 in PCT/FR09/051474 filed Jul. 22, 2009.
U.S. Appl. No. 13/003,065, filed Jan. 7, 2011, Ilekti, et al.
U.S. Appl. No. 12/988,465, filed Oct. 18, 2010, Ilekti, et al.
U.S. Appl. No. 13/009,975, filed Jan. 20, 2011, Ilekti, et al.

* cited by examiner

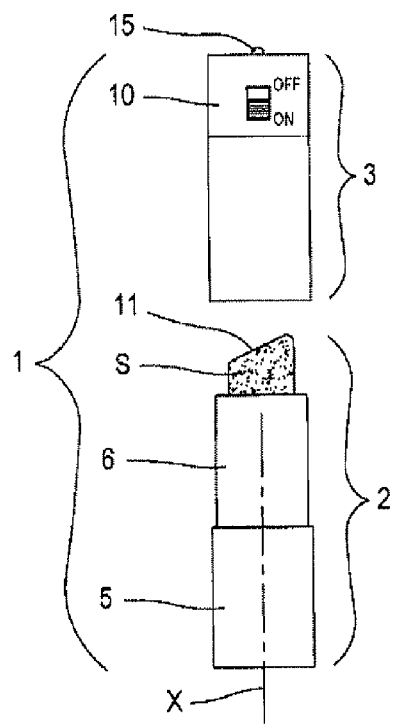
FIG. 1
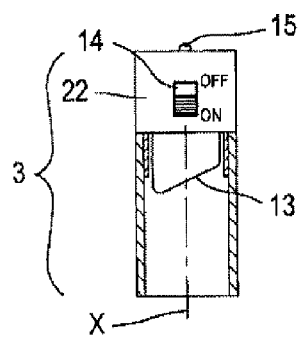
FIG. 2
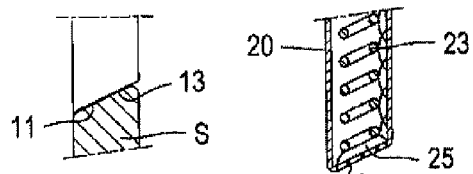
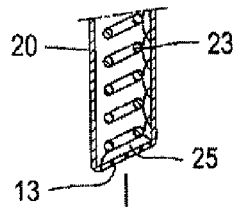
FIG. 3    FIG. 4
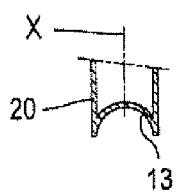
FIG. 5
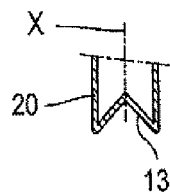
FIG. 6
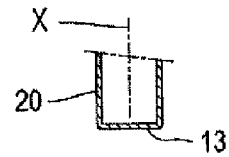
FIG. 7
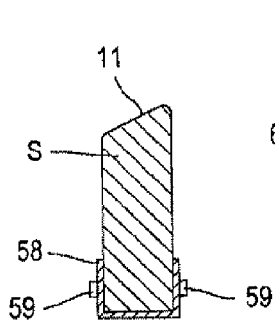
FIG. 10
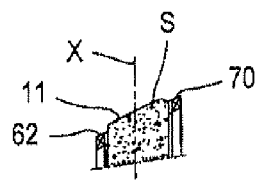
FIG. 12
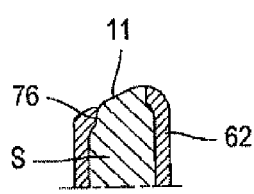
FIG. 13
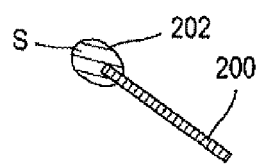
FIG. 14

COSMETIC HEAT TREATMENT METHOD

The present invention relates to the application of a cosmetic product to human keratinous materials, especially the skin or the lips.

More particularly, the invention relates to applying a product (also termed a "composition") initially in the form of a piece of solid product (also termed a "product mass"), especially a stick (also termed a "knob").

The present invention also pertains to solid cosmetic compositions for making up and/or for care of the skin and/or lips, procuring a glossy effect.

PRIOR ART

Lipsticks have long been packaged as sticks for direct application to the lips. In this case, the formulation of a lipstick must satisfy various requirements, on the one hand of a mechanical nature so that it can glide on and so that the stick is stable during application and to prevent it from breaking, and on the other hand of a transferring nature in order to guarantee comfortable application as well as a sufficient deposit, of the correct quality, on the lips.

These requirements are generally considered to be antagonistic and mean that restrictions are placed on the formulations which could usefully be relaxed.

Application US 2004/0 096 258 discloses a device for packaging and applying a lipstick that comprises a vibration generator and a heat generator. The vibration generator can be used to carry out a massaging action with a hot surface.

It is also known from European patent application EP 0 223 603 for stick lipsticks to undergo a flaming operation during manufacture thereof, consisting of briefly heating the surface of the stick in order to increase the surface gloss.

Application EP 1 595 472 A2 discloses a device comprising an electrical resistance for reshaping the application surface of a product contained in a body.

Heat is generally considered to be detrimental to the mechanical staying power of a product formed as a stick and thus U.S. Pat. No. 4,393,975 proposes a refrigeration device that can protect the stick from heat.

The publication US 2008/0 143 214 discloses a packaging device comprising a cap coated with a heating wire in order to heat up a stick of hair removal wax or a lipstick.

At the same time, in addition to the color which is the essential characteristic of a lipstick, users frequently desire gloss. While it is relatively easy to provide liquid formulae with gloss, this is much more difficult with a product in the form of a solid mass.

Thus, there is a need for providing a lipstick in the stick form with more gloss.

Many users would also like performance in terms of the staying power of the makeup.

However, the performances in terms of gloss and staying power are generally obtained by different, frequently antagonistic mechanisms.

Thus, there is a need for products to be available that can provide both gloss and staying power.

Finally, the sensory aspect is very important for products formed into sticks, because the user is only in contact with the product during application, especially as regards lipsticks, and the improvement in performances in terms of gloss and staying power cannot be obtained without having regard to this sensory aspect.

It is known that a certain number of ingredients that are capable of providing the product with advantageous characteristics in terms of gloss or staying power, for example, such as polymers, especially when they have a relatively high molecular weight, are detrimental to the application qualities or may even render application impossible.

The qualities of mechanical strength or heat resistance further complicate the formulator's task by rendering difficult the production of sticks with a weak structure with the aim of providing good transfer.

One known solution for incorporating certain compounds that are difficult to apply when cold consists of reducing the diameter of the stick, for example to 8 mm, and of providing a shaft around the stick on the case.

Such sticks used on such cases necessitate a lower wax content in order to provide them with staying power. However, consumers generally prefer fatter sticks with a diameter of more than 10 mm.

There exists a need for improving the performances of a product in the form of a solid mass both on the sensory level and/or as regards the finished makeup while retaining in the product mechanical properties that are compatible with packaging as a stick or in another solid form and with application by friction to the surface to be treated.

A need also exists for the development of a means that can be used to incorporate into a product all of the compounds necessary for producing properties of staying power and/or gloss that are satisfactory without, however, deleteriously affecting the application qualities of the product.

In particular, a need exists for the development of a means that can be used to incorporate into such a product one or more oils necessary for producing satisfactory gloss properties without deleteriously affecting the application qualities of the product.

It is known that a glossy character can conventionally be provided in this type of composition by using glossy oils, which are generally viscous. Using such compounds then generally affects the qualities of application comfort in particular in terms of glide. The addition of fluid oils, i.e. with a low viscosity, can certainly overcome this problem, but unfortunately may prove to be prejudicial because of the migratory nature of such oils.

Thus, a need exists for a mode of makeup that can exploit the high gloss of certain viscous oils without, however, requiring the use of compounds that could make up for such a high viscosity.

There also exists a need for a mode of makeup that allows the use of large quantities of high gloss viscous oils that up to now have not been considered because they have not been deemed to be compatible with good application quality.

More precisely, the invention proposes a novel mode of making up and/or skin care that can satisfy all of the requirements mentioned above.

Thus, in a first aspect, the present invention concerns a method for making up and/or for non-therapeutic care of non-fibrous human keratinous materials, in particular the skin, the mucous membranes or the nails, characterized in that an outer surface of a piece of solid cosmetic composition having a temperature-sensitive dynamic coefficient of friction equal to 0.5 or more at 25° C., more preferably equal to 0.6 or more at 25° C., is brought into contact with or into the vicinity of a heating device in order to heat said piece in a localized manner so as to soften essentially only said outer surface and to reduce the dynamic coefficient of friction thereof, in which method the outer surface of the thus heated composition is then applied to the region to be treated, and in particular to be made up, said composition being different from a composition in the form of a stick lipstick with a diameter of 12.7 mm, and in particular being defined as follows, the quantities being expressed as a percentage by weight

| | |
|---|---|
| BHT | 0.06 |
| PEG-45/DODECYL GLYCOL COPOLYMER | 6 |
| OCTYLDODECYL NEOPENTANOATE | 18 |
| POLYBUTENE | 15 |
| TRIISOSTEARIN | 7 |
| OCTYLDODECYL/PPG-3 MYRISTYL ETHER DIMER DILINOLEATE | 1 |
| BIS-DIGLYCERYL POLYACYLADIPATE-2 | 15 |
| ISOSTEARYL ISOSTERATE | 10 |
| DISTEARDIMONIUM HECTORITE | 1 |
| YELLOW 6 LAKE | 7 |
| RED 7 | 4 |
| TITANIUM DIOXIDE | 1 |
| POLYETHYLENE | 5 |
| MICROCRYSTALLINE WAX | 7 |
| MICA | 2.94 |

The piece of the composition may be permanently in contact with or in the proximity of the heating device which latter may be activated prior to application of the composition in order to raise the temperature of the outer surface of the piece of the composition. In a variation, the piece of the composition is only brought into contact with or into the proximity of the heating device for use, with a view to applying the composition.

In a variation, the composition under consideration in accordance with the invention comprises at least 10% by weight of glossy oil(s), said glossy oil being a hydrocarbon or silicone oil with a molecular mass of 400 g/ml or more.

Thus, in a further aspect, the present invention concerns a method for making up and/or for non-therapeutic care of non-fibrous human keratinous materials, in particular the skin, the mucous membranes or the nails, comprising at least the steps consisting of bringing an outer surface of a piece of solid cosmetic composition into contact with or into the vicinity of a heating device so as to heat said piece in a localized manner such that essentially only said outer surface is softened in particular with a view to reducing the dynamic coefficient of friction thereby; and then applying the outer surface of the composition heated thereby to the region to be treated, and in particular to be made up;

said composition comprising a quantity of 10% by weight or more of glossy oil(s) with respect to the total composition weight, said glossy oil being a hydrocarbon or silicone oil with a molecular mass of 400 g/ml or more.

In a particular implementation of the invention, the method is a method for making up.

In a variation, the composition under consideration of the invention comprises at least one hydrocarbon glossy oil in combination with less than 40% or even less than 30% by weight of a fluid oil, said fluid oil in particular having a molecular weight of less than 400 g/mol.

In a particular implementation, the softened outer surface is brought into direct contact with the region to be treated, in particular keratinous materials.

In other words, no applicator is employed for depositing the softened composition.

In accordance with a further aspect, the invention concerns a kit comprising:

a composition as hereinbefore defined; and a heating device that can locally heat a surface of a piece of said composition, the composition in particular being in the form of a stick with a diameter other than 12.7 mm.

In the context of the present invention, the term "solid", in particular at ambient temperature (for example at 20° C.) means a composition with a high consistency which retains its shape during storage; in particular, it does not flow under its own weight.

When the composition is in the form of a stick, the outer surface may be defined as the end thereof.

The invention means that the surface, for example the top of the bevel tip of a stick lipstick produced using a composition in accordance with the invention, can be heated just before application in order to allow deposition even if the stick contains compounds that are poorly suited to satisfactory application when cold, said compounds providing enhanced performances in terms of staying power and/or gloss.

In the implementational examples of the invention, by heating up the surface of the stick, its glide and thus its application to the lips or the skin can be improved.

Advantageously, the solid composition has a hardness of 80 $Nm^{-1}$ or more at 20° C., preferably 100 $Nm^{-1}$ or more, or even 120 $Nm^{-1}$ or more at 20° C., which renders the stick mechanically strong and means, for example, that it can be packaged in a conventional case comprising two portions that can turn with respect to each other in order to displace the stick.

The dynamic coefficient of friction may be 0.45 or less, preferably 0.4 or less at the temperature to which the composition is heated.

The dynamic coefficient of friction that is 0.5 or more at 25° C. may thus, for example, become 0.45 or less at 45° C., i.e. reach a value comparable with certain known lipsticks intended for application at 25° C.

The invention is applicable to a stick of product with a texture such that its application when cold is difficult and/or which comprises glossy polymers which are almost impossible to apply or application is disagreeable without heating. For such a stick of product, application after heating becomes possible, with superior performances as regards gloss.

With the invention, a composition can be packaged in the form of a stick, for example with a diameter of 7 mm or more, preferably with a relatively large diameter, for example 10 mm or more, for example 50 mm or less, without problems as regards staying power or product transfer, since the structuring compounds introduced, which are problematic to cold application, are less so when the temperature is increased.

The product may be a product for application to the lips, especially a lipstick or a lip gloss. The products concerned by the invention are not, however, limited to makeup products, and the invention also concerns non-therapeutic skin care products.

The product may be heated in a variety of manners, for example by being exposed to infrared radiation or to radio-electrical radiation.

The product may also be heated by blowing hot air, by being exposed to ultrasound vibrations or by heat transfer in contact with or in the proximity of a hot surface which, for example, is applied radially against the outer surface, in particular the end of a stick. The hot surface may also come into contact axially against the outer surface, in particular the end of the stick. The hot surface may have the shape of a bevel tip, an inverted cone or be concavely dished, in particular spherical.

The piece of product, especially the stick, may pass through the hot surface; to this end, it may be annular in shape.

The piece of product may be in the form of a stick, with the hot surface coming into contact with or facing the end face of the stick, for example.

Heating may take place only at the end of the stick, whereupon the hot surface does not, for example, cover the lateral surface of the stick.

The piece of product may initially be molded into the desired shape, for example into the shape of a stick, with no armature, as is the case with conventional lipsticks, or onto an armature and/or a grasping portion, being supported at the end of a wand, for example.

The product may be heated while the piece of product is entirely contained in a packaging device.

During application, the user's fingers do not need to come into contact with the product.

The product may be heated while the piece of product is at least partially exposed to ambient air.

The outer surface of the product may be heated to a temperature $T_f$ of 40° C. or more, or even 45° C. or more, more preferably 50° C. or more. The outer surface may be heated to a temperature $T_f$ in the range 40° C. to 95° C., preferably in the range 45° C. to 85° C., or more preferably in the range 45° C. to 75° C. The temperature of the application surface, in particular the end of the stick, must not be such as to run the risk of burning upon application. For this reason, a delay may possibly be necessary between the time at which the end is heated and application to the keratinous materials.

The temperature difference between the heated outer surface and the portion of the product that remains solid may be 5° C. or more, or preferably 15° C. or 20° C. or more, at least at the start of application, or even 30° C. or more.

Only the product can come into contact with the treated region during application.

During application, the piece of product may remain integral with a base portion comprising a mechanism that can displace the product mass relative to a surface of the base portion intended to be grasped by the user, especially a mechanism comprising two parts that can rotate with respect to each other.

The outer surface softened by the heating device may be supported by the piece of cosmetic composition that is solid at the moment of application. In a variation, the softened outer surface may be supported differently, after transfer onto a support serving for application. Thus, in one implementational example of the invention, the product may be heated and removed with an applicator or a finger in order to apply it to the skin or lips. The piece of product may be contained in a cup and the upper surface of the product present in the cup may then be heated up.

The heating device may or may not remain integral with the piece of cosmetic composition that is solid at the moment of application of the softened outer surface to the human keratinous materials.

In another aspect, the invention pertains to a device for packaging and application of a product in the form of a solid piece, especially a stick, comprising:
  a support for said piece of solid product, this latter having an outer surface, especially an end;
  a heating device that is integral with or that can be rendered integral with the packaging and application device, in contact with or which can be brought into contact with or into the vicinity of said outer surface in order to heat said piece in a localized manner, in order to soften essentially only said outer surface, for example over a depth of 0.5 mm to 5 mm, preferably 0.5 mm to 2 mm.

In other words, especially in the case of heat transfer by conduction, convection or infrared radiation, the heat is not transmitted to the application surface from the core of the piece of the product, but from the outside.

Advantageously, as mentioned above, the product may have a dynamic coefficient of friction of 0.5 or more at 25° C., preferably 0.6 or more at 25° C.

The heating device may be housed in a cap closure of the support in order to allow the outer surface to be heated with the cap in place on the support. The heating device may also be housed elsewhere than in the cap closure of the support.

The heating device may be accommodated in a housing onto which the support may be engaged such that heating can take place when the support is engaged in the housing, especially a housing comprising an opening into which the piece of solid product can be engaged, preferably without the entirety of the support being disposed inside the housing.

The heating device may be integral with the device for packaging and application.

The heating device may be arranged to come into contact with the outer surface.

The heating device may be arranged so that the piece of product can pass through it; in particular, it may comprise a hot surface which is annular in shape.

The heating device may comprise a control means allowing the user to control its operation. This control means may comprise a switch present on the support or on a cap closure of the support.

The heating device may comprise an electrical resistance to heat a surface that can come into contact with or into the proximity of the application surface.

The heating device may comprise an infrared emitter arranged to subject the application surface to infrared light in order to heat it, a means for emitting radioelectrical radiation that can raise the temperature of the outer surface, a fan to blow hot air onto the outer surface or a source of ultrasound to heat up the outer surface.

The heating device may also comprise at least two components that are capable of producing an exothermic reaction when mixed.

The piece of product may be in the shape of a stick and the outer surface may be defined by the end of the stick.

The heating device may comprise a source of electrical energy comprising one or more storage batteries or cells.

The heating device may comprise an electrical generator actuated by the user.

The heating device may comprise means for heating the piece of the composition to a pre-defined temperature despite wear of said piece. This means may comprise an elastically deformable member that ensures contact with or a constant distance between the outer surface to be heated and the heating device, compensating for wear of the piece of the composition.

If appropriate, these means may also comprise a temperature sensor that can be used to adjust the heating power, for example to increase it if the outer surface is further from the heat source.

In a further aspect, the invention also pertains to a method for making up and/or for non-therapeutic care of non-fibrous human keratinous materials, in particular the skin, the mucous membranes or the nails, comprising the steps consisting of
  heating up an outer surface of a piece of a solid cosmetic composition having a hardness of 80 $Nm^{-1}$ or more in contact with or in the vicinity of a heating device in order to heat said piece in a localized manner;
  applying the composition heated thereby to the region to be treated, in particular for making up.

Dynamic Coefficient of Friction

In order to characterize the dynamic coefficient of friction of the product, an apparatus may be used comprising a carriage which is displaced over a length of 100 mm on ball bearings.

Proper displacement of the carriage is ensured by means of a rigid linkage to the moving beam of a traction and compression machine (TAXT2 from the supplier Rheo) placed in the horizontal position via a magnet fixed to the rear of the carriage.

The product S, the dynamic coefficient of friction of which is to be determined, is cut at one end with a tungsten wire with a diameter of 250 µM by displacing the wire relative to the stick at a rate of 100 min/min and perpendicular to its longitudinal axis in order to have a contact surface that is flat and parallel to the sliding surface W.

A force Fn normal to the sliding surface W is applied to it using a weight. This weight is such that the pressure exerted on the surface of the product S in contact with W is $7.9 \times 10^{-3}$ MPa.

The product may be in the form of a stick that is a cylindrical body of revolution.

In the case in which the cross section of the stick is not circular, the stick is caused to slide in the direction of the minor axis of its section, displacing the major axis parallel thereto.

The coefficient of friction is defined as the ratio of the tangential force Ft applied to the body caused to move in the direction M over the normal force Fn to which that body is subjected, as illustrated in FIG. 15.

In a friction test, a first transitional phase when the motion of the system is starting up can be distinguished from a second phase under steady conditions.

In the first phase, the tangential force increases to a maximum that corresponds to the system beginning to move. This maximum corresponds to the static frictional force, termed static Ft, and can be used to define a static coefficient of friction ($\mu s$):

$$\mu s = \text{static } Ft/Fn$$

where Fn is the normal force applied.

The tangential force Ft then decreases and generally reaches a more stable regime. The dynamic coefficient of friction is defined in this phase of movement as the ratio of the dynamic frictional force (tangential force) over the normal force applied (Fn):

$$\mu d = \text{dynamic } Ft/Fn$$

The coefficient of friction is a dimensionless quantity, a function of the two surfaces in contact and the contact conditions.

The sliding surface is defined by artificial skin with reference "BIO SKIN Plate Black K275" from the supplier MACREPOS, with a width equal to or greater than that of the section of the stick.

For a measurement at 25° C., the assembly formed by the apparatus and the composition is at 25° C.

The artificial skin is placed on a support that may be heated to the temperature at which the dynamic coefficient of friction is to be measured. As an example, the stick initially at a temperature of 25° C. is applied to the artificial skin heated, for example, to 45° C. if the measurement is to be carried out at 45° C. The temperature of the surface of the artificial skin may be monitored with an optical thermometer.

In certain embodiments, the dynamic coefficient of friction of a composition of the invention is 0.6 or more, or even 0.7 or 0.8, at 25° C. The dynamic coefficient of friction at 25° C. of the compositions of the invention may be 5 or less.

The stick may have a diameter of 12.7 mm at its contact zone with the sliding surface, but other values are possible, for example from 7 mm to 50 mm.

Hardness Parameter

The invention is of advantageous application to compositions that are relatively hard at ambient temperature and which become sufficiently soft under the action of heat to be applicable.

The hardness may be measured at 20° C. using the "cheese-wire" method, which consists of transversely cutting a stick of product, preferably a cylindrical body of revolution, using a rigid tungsten wire with a diameter of 250 µm by displacing the wire relative to the stick at a rate of 100 mm/min. The hardness corresponds to the maximum shear force created by the wire on the stick at 20° C., that force being measured using a DFGHS 2 dynamometer from the supplier Indelco-Chatillon. The measurement is carried out three times then averaged.

The mean of the three values recorded using the dynamometer mentioned above, denoted Y, is given in grams. This mean is converted into Newtons then divided by L, which represents the largest dimension passed through by the wire. In the case of a cylindrical stick, L is equal to the diameter in meters.

The hardness is converted using the equation below:

$$(Y \times 10^{-3} \times 9.8)/L$$

For a measurement at a different temperature, the whole stick is heated to the temperature at which the hardness is to be measured.

In accordance with this method, the hardness at 20° C. of examples of the composition in accordance with one aspect of the invention is greater than 80 Nm$^{-1}$, in particular greater than 100 Nm$^{-1}$, preferably greater than 120 Nm$^{-1}$.

A composition of the invention is cosmetically or dermatologically acceptable, i.e. it contains a non-toxic physiologically acceptable medium that is capable of being applied to the lips of human beings. The term "cosmetically acceptable" as used in the context of the invention means a composition with an agreeable appearance, odor and feel, suitable for use in cosmetics.

In accordance with a variation, the cosmetic compositions under consideration of the invention further contain at least one colorizing agent. As will be defined below, this definition covers any organic or inorganic material that is capable of procuring a colored and/or optical effect.

In accordance with another variation, the compositions of the invention may advantageously comprise at least 30% by weight of a fatty phase with respect to the total composition weight, especially at least 50% by weight, or even at least 70% by weight.

In accordance with another variation, the compositions of the invention comprise a fatty phase containing at least 5%, in particular at least 7% and especially at least 10% by weight of solid fats with respect to the total weight of the fatty phase, or even at least 20% by weight, or furthermore at least 30% by weight.

The term "solid" characterizes the state of the composition at ambient temperature (25° C.) and at atmospheric pressure (760 mm Hg).

Oil

The oil may be selected from any cosmetically acceptable oils, especially mineral, vegetable or synthetic oils; in particular hydrocarbon and/or silicone and/or fluorinated oils, volatile or non-volatile, and mixtures thereof.

In the context of the present invention, the term "silicone oil" means an oil comprising at least one silicon atom, and in particular at least one Si—O group.

The term "fluorinated oil" means an oil comprising at least one fluorine atom.

More precisely, the term "hydrocarbon oil" means an oil principally comprising atoms of carbon and hydrogen and optionally one or more functions selected from hydroxyl, ester, ether and carboxyl functions.

Glossy Oil

A composition according to the invention advantageously contains at least one glossy oil.

More precisely, the term "glossy oil" in the context of the invention means a hydrocarbon or silicone oil with a molecular mass of more than 400 g/mol, or even more than 500 g/mol, especially more than 650 g/mol. In particular, said glossy oil may have a molar mass of 400 to 10 000 g/mol, in particular 650 to 10 000 g/mol and more particularly 650 to 5 000 g/mol.

In particular, a composition comprises a sufficient quantity of glossy oil(s) to produce at least gloss type makeup performance.

A composition of the invention may comprise a glossy oil(s) content of 10% to 80%, for example 15% to 70% by weight, preferably 20% to 60% and more preferably 25% to 60% by weight, or even 30% to 60% by weight, with respect to the total composition weight.

This glossy oil may be polar or apolar.

This glossy oil is advantageously an oil selected from high molar mass oils, in particular with a molar mass of 500 to 10 000 g/mol, in particular 500 to 8 000 g/mol and more particularly 550 to 7 500 g/mol Preferably, the glossy oil has a refractive index of 1.45 or more, in particular from 1.45 to 1.6.

The glossy oil is preferably a non-volatile oil.

Advantageously, a hydrocarbon glossy oil that may be used in the present invention may be selected from:

lipophilic polymers such as:
polybutylenes such as, for example, INDOPOL H-100 (with a molar mass or MW=965 g/mol), INDOPOL H-300 (MW=1340 g/mol), or INDOPOL 1500 (MW=2160 g/mol), sold or manufactured by the supplier AMOCO;
hydrogenated polyisobutylenes such as, for example, PANALANE H-300 E sold or manufactured by the supplier AMOCO (MW=1340 g/mol), VISEAL 20000 sold or manufactured by the supplier SYNTEAL (MW=6000 g/mol), or REWOPAL PIB 1000 sold or manufactured by the supplier WITCO (MW=1000 g/mol);
polydecenes and hydrogenated polydecenes such as, for example: PURESYN 10 (MW=723 g/mol) or PURESYN 150 (MW=9200 g/mol), sold or manufactured by the supplier MOBIL CHEMICALS;
vinylpyrrolidone copolymers such as, for example: vinylpyrrolidone/1-hexadecene copolymer, ANTARON V-216 sold or manufactured by the supplier ISP (MW=7300 g/mol);

esters such as:
esters of linear fatty acids with a total carbon number of 35 to 70 such as, for example, pentaerythrityl tetrapelargonate (MW=697 g/mol);
hydroxylated esters such as, for example, polyglyceryl-2 triisostearate (MW=965 g/mol), triisocetyl citrate (MW=864 g/mol), or diisostearyl malate (MW=639 g/mol) such as that sold under the trade name Schercemol DISM by the supplier Lubrizol;
aromatic esters such as, for example, tridecyl trimellitate (MW=757 g/mol);
esters of branched $C_{24}$-$C_{28}$ fatty alcohols or fatty acids such as, for example, those described in application EP-A-0 955 039, and especially triisoarachidyl citrate (MW=103176 g/mol), or pentaerythrityl tetraisononanoate (MW=697 g/mol), glyceryl triisostearate (MW=891 g/mol), or glyceryl tri 2-decyl tetradecanoate (MW=1143 g/mol), pentaerythrityl tetraisostearate (MW=1202 g/mol), polyglyeeryl-2 tetraisostearate (MW=1232 g/mol) or pentaerythrityl 2-tetradecyl tetradecanoate (MW=1538 g/mol);
a polyester resulting from esterification of at least one carboxylic acid triglyceride hydroxylated by an aliphatic monocarboxylic acid and by an aliphatic dicarboxylic acid, possibly unsaturated such as, for example, castor oil, succinic acid and isostearic acid sold under the reference Zenigloss by Zenitech;
dimeric diol and dimeric diacid esters with general formula: HO—$R^1$—(—OCO—$R^2$—COO—$R^1$—)$_h$—OH, wherein:
$R^1$ represents a dimeric diol residue obtained by hydrogenation of dilinoleic diacid;
$R^2$ represents a hydrogenated dilinoleic diacid residue; and
h represents a whole number from 1 to 9;
especially esters of dilinoleic diacids and dilinoleic dimeric dials sold by the supplier NIPPON FINE CHEMICAL under the commercial trade name LUSPLAN DD-DA5® and DD-DA7®;
oils of vegetable origin such as sesame oil, for example (MW=820 g/mol);
and mixtures thereof.

The hydrocarbon glossy oil may also be an oligomer of a hydroxylated fatty acid triglyceride and saturated diacid.

Such an oligomer is obtained by reaction of a hydroxylated fatty acid triglyceride (such as hydrogenated castor oil) and a saturated diacid.

According to the invention, the diacid is termed saturated when the hydrocarbon chain constituting it does not include an unsaturated bond, namely a carbon-carbon double bond. The term diacid means a hydrocarbon compound comprising two carboxyl functions —COOH. The diacid may be a single diacid or a mixture of several diacids.

Similarly, in the context of the invention, the oligomer may be a mixture of several oligomers.

Examples of saturated diacids that may be used that may be cited are sebacic acid (or 1,10-decanedioic acid), succinic acid, adipic acid, azelaic acid, octadecamethylene dicarboxylic acid and eicosadicarboxylic acid.

More particularly, the oligomer may be an oligoester wherein the monomers are represented by the following triglyceride (A) and diacid (B) formulae:

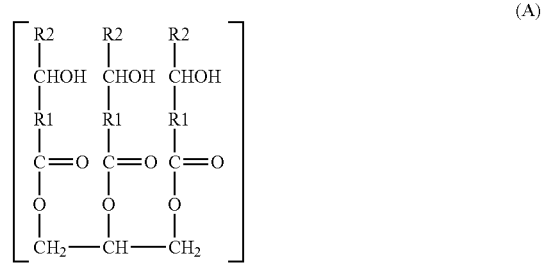

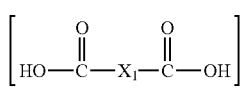

wherein:

$R_1$ represents a saturated or unsaturated, linear or branched alkylene group containing 1 to 18 carbon atoms, for example, and $R_2$ represents a saturated or unsaturated, linear or branched alkyl group containing 1 to 12 carbon atoms, for example;

$R_1$ preferably represents a —$(CH_2)_n$—, group where n can be between 1 and 20 and especially between 3 and 16, for example between 6 and 12;

$R_2$ preferably represents a —$(CH_2)_m CH_3$ group, where m can be between 0 and 11 and especially between 2 and 11, for example between 3 and 9;

In one embodiment, n=10 and m=5, and the group

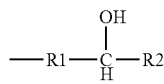

represents the alkyl residue of 12-hydroxystearic acid (major component of hydrogenated castor oil);

$X_1$ is a linear or branched alkylene group such as, for example, a linear alkylene group —$(CH_2)_x$—, where x can be between 1 and 30 and especially between 3 and 15.

When the diacid is sebacic acid, x is equal to 8.

The mean degree of polymerization of the oligomer may be between 3 and 12.

The oligoester of hydrogenated castor oil and sebacic acid is sold in particular by the supplier CRODA under various denominations depending on the degree of polymerization.

Of the oligoesters formed by hydrogenated castor oil and sebacic acid, that with a degree of polymerization of approximately 4.6 is available under the commercial name "CROMADOL CWS-5" and that with a degree of polymerization of approximately 9.5 is available under the commercial name "CROMADOL CWS-10", sold by Croda Japan K.K.

It is also possible to cite the oligomer of hydrogenated castor oil and sebacic acid sold under the name CRODA-BOND-CSA (PM=3500) by the supplier CRODA.

The glossy oil may also be an oil selected from silicone oils such as polydimethylsiloxanes (PDMS); phenylated silicones such as phenyl trimethicones (such as the phenyl trimethicone sold under the commercial name DC556 by Dow Corning), phenyl dimethicones, phenyl trimethylsiloxy diphenyl siloxanes, diphenyl dimethicones, diphenyl methyldiphenyl trisiloxane, trimethyl pentaphenyl trisiloxane (especially 1,3,5-trimethyl 1,1,3,5,5-pentaphenyl trisiloxane sold under the name PH-1555 HRI by Dow Corning) and mixtures thereof.

Preferably, it is a hydrocarbon oil.

Fluid Oil

As will be apparent from the foregoing, it is generally necessary to combine a more fluid oil with a glossy oil provided with a high viscosity, in order to guarantee satisfactory deposition qualities for the corresponding composition. However, under certain circumstances these fluid oils, precisely because of their fluidity, can suffer from a migration phenomenon which is detrimental to the quality of the makeup. In particular, the contours of a film of makeup lose sharpness because of the tendency of certain of those oils to diffuse.

The invention can limit the use of such fluid oils in compositions requiring the presence of glossy oil(s).

In the context of the invention, the expression "fluid oil" denotes an oil with a molecular mass of less than 400 g/mol, in particular between 100 and 390 g/mol.

This oil may or may not be volatile.

It may be a hydrocarbon or silicone oil.

The term "volatile oil" as used in the context of the invention means an oil that is capable of evaporating on contact with the skin or the keratinous fiber in less than one hour, at ambient temperature and atmospheric pressure. The volatile oils of the invention are volatile cosmetic oils, which are liquid at ambient temperature, having a non-zero vapor pressure at ambient temperature and atmospheric pressure, in particular from 0.13 Pa to 40 000 Pa ($10^{-3}$ to 300 mm Hg), in particular 1.3 Pa to 13 000 Pa (0.01 to 100 mm Hg), and more particularly 1.3 Pa to 1300 Pa (0.01 to 10 mm Hg).

The term "non-volatile oil" means an oil remaining on the skin or the keratinous fiber at ambient temperature and atmospheric pressure for at least a few hours and in particular having a vapor pressure of less than $10^{-3}$ mm Hg (0.13 Pa).

A composition of the invention may comprise less than 2%, or even less than 1% of volatile oil, or it may be completely free of volatile oil.

Examples of fluid oil that may be used in the invention that may be cited are:

volatile hydrocarbon oils selected from hydrocarbon oils containing 8 to 16 carbon atoms, and especially branched $C_8$-$C_{16}$ alkanes such as $C_8$-$C_{16}$ isoalkanes of oil origin (also termed isoparaffins) such as isododecane (also termed 2,2,4,4,6-pentamethylheptane), isodecane, isohexadecane, and for example the oils sold under the commercial names Isopars or Permethyls, branched $C_8$-$C_{16}$ esters, iso-hexyl neopentanoate, and mixtures thereof. Other volatile hydrocarbon oils such as oil distillates, especially those sold under the trade name Shell Solt by the supplier SHELL, may also be used;

volatile silicones such as, for example, linear or cyclic volatile silicone oils, especially those with a viscosity of ≤8 centistokes ($8\times10^{-6}$ m²/s), and in particular containing 2 to 6 silicon atoms, said silicones optionally comprising alkyl or alkoxy groups containing 1 to 10 carbon atoms. Examples of volatile silicone oils that may be used in the invention that may in particular be cited are octamethyl cyclotetrasiloxane, heptamethyloctyl trisiloxane, hexamethyl disiloxane, octamethyl trisiloxane and decamethyl tetrasiloxane;

synthesized esters, in particular from fatty acids such as oils with formula $R_1COOR_2$ wherein $R_1$ represents the residue of a linear or branched higher fatty acid containing 1 to 30 carbon atoms and $R_2$ represents a hydrocarbon chain, in particular branched, containing 1 to 30 carbon atoms with $R_1+R_2<30$ such as, for example, Purcellin oil (cetostearyl octanoate), isononyl isononanoate, isopropyl myristate, isopropyl palmitate, $C_{12}$ to $C_{15}$ alcohol benzoate, hexyl laurate, diisopropyl adipate, ethyl 2-hexyl palmitate, isostearyl isostearate; octanoates, decanoates or ricinoleates of alcohols or polyalcohols such as propylene glycol dioctanoate; hydroxylated esters such as isostearyl lactate, octyl hydroxystearate; polyol esters such as propylene glycol dioctanoate, neopentyl glycol diheptanoate, or diethylene glycol diisononanoate;

fatty alcohols that are liquids at ambient temperature with a branched and/or saturated carbonaceous chain containing 8 to 26 carbon atoms such as oleic alcohol, linoleic or linolenic alcohol, isostearic alcohol or octyl dodecanol such as that sold under the commercial reference Eutanol G® by the supplier Cognis;

higher fatty acids such as oleic acid, linoleic acid, linolenic acid;

carbonates;

acetates;

citrates;

silicone oils such as polydimethylsiloxanes (PDMS);

and mixtures thereof.

More particularly, a composition in accordance with the invention comprises less than 30% by weight, advantageously less than 25% by weight, and more particularly less than 20% by weight of fluid oil(s), in particular linear or branched hydrocarbon(s) and/or fatty alcohol(s) that are liquid at ambient temperature with a branched and/or unsaturated carbon chain containing 8 to 26 carbon atoms.

Advantageously, the compositions containing at least one glossy oil, in particular in an amount of at least 10% by weight, may contain less than 30% by weight, in particular less than 20% by weight of fluid oil(s) with respect to the total composition weight.

Further, the compositions containing at least one glossy oil may comprise it in a glossy oil(s)/fluid oil(s) weight ratio of more than 0.5, in particular more than 1.

Fatty Phase

A composition in accordance with the invention thus comprises at least one fatty phase, for example in an amount of at least 20% by weight, in particular at least 30% by weight, especially at least 40% by weight, or even at least 60% by weight with respect to its total weight. This phase may contain at least one solid fat selected from waxes and pasty compounds.

The fatty phase generally comprises at least one oil and/or at least one wax.

A composition in accordance with the invention may also contain one or more solid fats, especially in an amount of at least 5% by weight, in particular at least 10% by weight with respect to its total weight.

These solid fats may be selected from waxes, pasty compounds and mixtures thereof.

Wax

In general, the wax under consideration in the context of the present invention is a lipophilic compound, solid at ambient temperature (25° C.), with a reversible solid/liquid change of state, having a melting point of 30° C. or more possibly up to 200° C. and in particular up to 120° C.

In accordance with one embodiment of the invention, hair removal waxes are excluded as waxes suitable for implementing the invention.

In particular, the waxes suitable for the invention may have a melting point of 45° C. or more, in particular 55° C. or more.

In the context of the invention, the temperature of melting corresponds to the temperature of the most endothermic peak observed in thermal analysis (DSC) as described in ISO standard 11357-3; 1999. The melting point of the wax may be measured using a differential scanning calorimeter (DSC), for example the calorimeter sold under the trade name "MDSC 2920" by the supplier TA Instruments.

The measurement protocol is as follows:

A 5 mg sample of wax disposed in a crucible is subjected to a first temperature rise from −20° C. to 100° C. at a heating rate of 10° C./minute and then is cooled from 100° C. to −20° C. at a cooling rate of 10° C./minute, and finally undergoes a second temperature rise from −20° C. to 100° C. at a heating rate of 5° C./minute. During the second temperature rise, the variation in the difference in the power absorbed by the empty crucible and by the crucible containing the wax sample is measured as a function of temperature. The melting point of the compound is the value of the temperature corresponding to the crest of the peak of the curve representing the variation in the absorbed power difference as a function of temperature.

The waxes that may be used in the compositions of the invention are selected from waxes that are solid at ambient temperature of animal, vegetable, mineral or synthesized origin, and mixtures thereof.

[1] Illustrative examples of waxes suitable for use in the invention that may in particular be cited are hydrocarbon waxes such as beeswax, lanolin wax and Chinese insect waxes, rice waxes, carnauba wax, candellila wax, ouricurry wax, alfa wax, berry wax, shellac wax, Japanese wax and sumac wax, montan wax, orange and lemon waxes, micro-crystalline waxes (such as that sold under the reference Microwax HW by the supplier Paramelt), paraffins and ozokerite; polyethylene waxes such as those sold under the trade name Performalene 500-L and Performalene 400 by the supplier New Phase Technologies, and waxes obtained by Fischer-Tropsch synthesis.

It is also possible to cite waxes obtained by catalytic hydrogenation of animal or vegetable oils containing linear or branched $C_8$-$C_{32}$ fatty chains. Particular examples of these that may be cited are isomerized jojoba oil such as trans-isomerized partially hydrogenated jojoba oil manufactured or sold by the supplier DESERT WHALE under the commercial reference Iso-Jojoba-50®, hydrogenated sunflower seed oil, hydrogenated castor oil, hydrogenated coprah oil, hydrogenated lanolin oil and di-(1,1,1-trimethylol propane) tetrastearate sold under the trade name Hest 2T-4S® by the supplier HETERENE.

It is also possible to cite silicone waxes ($C_{30-45}$ ALKYL DIMETHICONE), and fluorinated waxes.

It is also possible to cite waxes obtained by hydrogenating castor oil esterified with cetyl alcohol sold under the trade names Phytowax ricin 16L64® and 22L73® by the supplier SOPHIM. Such waxes are described in application FR-A-2 792 190.

Examples of waxes that may be used are a $C_{20}$-$C_{40}$ alkyl (hydroxystearyloxy)stearate (the alkyl group containing 20 to 40 carbon atoms), alone or as a mixture. In particular, such a wax is sold under the trade names "Kester Wax K 82 P®", "Hydroxypolyester K 82 P®" and "Kester Wax K 80®", and "Kester Wax K 82 H®" by the supplier KOSTER KEUNEN.

Examples of microwaxes that may be used in the compositions of the invention that may in particular be cited are carnauba microwaxes such as that sold under the trade name MicroCare 350® by the supplier MICRO POWDERS, synthetic wax microwaxes such as that sold under the trade name MicroEase 114S® by the supplier MICRO POWDERS, microwaxes constituted by a mixture of carnauba wax and polyethylene wax such as those sold under the trade names Micro Care 300® and 310® by the supplier MICRO POWDERS, microwaxes constituted by a mixture of carnauba wax and synthetic wax such as that sold under the trade name Micro Care 325® by the supplier MICRO POWDERS, polyethylene microwaxes such as those sold under the trade names Micropoly 200®, 220®, 220L® and 250S® by the supplier MICRO POWDERS and polytetrafluoroethylene microwaxes such as those sold under the trade names Microslip 519® and 519 L® by the supplier MICRO POWDERS.

The composition in accordance with the invention may comprise a wax content in the range 0.1% to 50% by weight, in particular 0.1% to 45% by weight, for example 2% to 35% by weight, 4% to 30% by weight, or in certain embodiments in the range 4% to 15% by weight, with respect to the total composition weight.

Pasty Compounds

The composition of the invention may also comprise at least one pasty compound.

The term "pasty" in the context of the present invention means a lipophilic fat with a reversible solid/liquid change of state having an anisotropic crystalline organization in the solid state and comprising a liquid fraction and a solid fraction at a temperature of 23° C.

In other words, the starting temperature of melting of the pasty compound may be less than 23° C. The liquid fraction of the pasty compound measured at 23° C. may represent 9% to 97% of the weight of the compound. This liquid fraction at 23° C. preferably represents in the range 15% to 85%, more preferably in the range 40% to 85% by weight.

The liquid weight fraction of the pasty compound at 23° C. is equal to the ratio of the enthalpy of melting consumed at 23° C. over the enthalpy of melting of the pasty compound.

The enthalpy of melting of a pasty compound is the enthalpy consumed by the compound on passing from the solid state to the liquid state. The pasty compound is said to be in the solid state when the whole of its mass is in the solid form. The pasty compound is said to be in the liquid state when the whole of its mass is in the liquid form.

The enthalpy of melting of a pasty compound is equal to the area under the curve of the thermogram obtained using a differential scanning calorimeter (DSC) such as the calorimeter sold under the trade name MDSC 2920 by the supplier TA Instruments, with a temperature rise of 5° C. or 10° C. per minute, in accordance with the ISO standard 11357-3: 1999. The enthalpy of melting of a pasty compound is the quantity of energy necessary to change the compound from the solid state to the liquid state. It is expressed in J/g.

The enthalpy of melting consumed at 23° C. is the quantity of energy absorbed by the sample in passing from the solid state to the state it is in at 23° C. constituted by a liquid fraction and a solid fraction.

The liquid fraction of a pasty compound measured at 32° C. preferably represents 30% to 100% of the weight of the compound, preferably 50% to 100%, more preferably 60% to 100% by weight of the compound. When the liquid fraction of the pasty compound measured at 32° C. is equal to 100%, the temperature of the end of the melting range of the pasty compound is 32° C. or less.

The liquid fraction of the pasty compound measured at 32° C. is equal to the ratio of the enthalpy of melting consumed at 32° C. over the enthalpy of melting of the pasty compound. The enthalpy of melting consumed at 32° C. is calculated in the same manner as the enthalpy of melting consumed at 23° C.

The pasty compound is preferably selected from synthetic compounds and compounds of vegetable origin. A pasty compound may be obtained by synthesis from starting products of vegetable origin.

The pasty compound may advantageously be selected from:
i) lanolin and its derivatives;
ii) polymeric or non-polymeric silicone compounds;
iii) polymeric or non-polymeric fluorinated compounds;
iv) vinyl compounds, in particular:
homopolymers and copolymers of olefins;
homopolymers and copolymers of hydrogenated dienes;
linear or branched oligomers, homo- or copolymers of alkyl(meth)acrylates preferably having a $C_8$-$C_{30}$ group;
vinylpyrrolidone/eicosene copolymers (INCI name VP/eicosene copolymer), for example sold by the supplier ISP under the commercial name Ganex V220F®;
homo- and copolymeric oligomers of vinylethers containing $C_8$-$C_{30}$ alkyl groups;
liposoluble polyethers resulting from polyetherification between one or more $C_2$-$C_{100}$ diols, preferably $C_2$-$C_{50}$;
v) esters,
vi) and mixtures thereof.

Particularly preferred esters are:
esters of an oligomeric glycerol, especially esters of diglycerol, in particular condensates of adipic acid and glycerol, wherein a portion of the hydroxyl groups of the glycerols have reacted with a mixture of fatty acids such as stearic acid, capric acid, stearic acid and isostearic acid and 12-hydroxystearic acid, in particular in the manner of bis diglyceryl polyacyladipate-2, in particular such as that sold under the trade mark Softisan 649® by the supplier Sasol;
arachidyl propionate sold under the trade mark Waxenol 801 by Alzo;
esters of phytosterol;
triglycerides of fatty acids and derivatives thereof;
esters of pentaerythritol;
non-cross-linked polyesters resulting from polycondensation between a dicarboxylic acid or a linear or branched $C_4$-$C_{50}$ carboxylic polyacid and a $C_2$-$C_{50}$ diol or polyol;
aliphatic esters resulting from the esterification an aliphatic hydroxycarboxylic acid by an aliphatic carboxylic acid;
esters resulting from the esterification of an aliphatic acid and a hydroxylated aliphatic ester. These esters may result from esterification a) of a monocarboxylic or polycarboxylic aliphatic acid, and b) of a hydroxylated aliphatic ester, in particular a hydroxycarboxylic acid ester;
dimeric diol and dimeric diacid esters, if necessary esterified on their free alcohol or acid function(s) by acid or alcohol radicals such as bis-behenyl/isostearyl/phytosteryl dimer dilinoleyl dimer sold in particular under the commercial name Plandool-G® by the supplier Nippon Fine Chemical;
and mixtures thereof.

Examples of preferred pasty compounds which may be selected are vinylpyrrolidone/eicosene copolymer, bis-behenyl/isostearyl/phytosteryl dimer dilinoleyl dimer, bis-diglyceryl polyacyladipate-2, hydrogenated castor oil dimer dilinoleate, for example RISOCAST-DA-L sold by KOKYU ALCOHOL KOGYO, hydrogenated castor oil isostearate, for example SALACOS HCIS (V-L) sold by NISSHIN OIL, or a mixture thereof.

Preferably, the composition comprises a total quantity of pasty fats of more than 5% by weight, in particular more than 10% by weight, or even more than 20% by weight with respect to the total composition weight. In particular, the quantity of pasty fat may be from 5% to 80% by weight, especially 20% to 80% by weight, or even in certain embodiments 35% to 80% by weight, with respect to the total composition weight.

The compositions may also comprise at least one additional polymer.

Additional Polymer

The compositions of the invention may contain an additional polymer, which may or may not be film-forming.

In accordance with the present invention, the term "film-forming polymer" means a polymer that can, of itself or in the presence of an auxiliary film-forming agent, form a macroscopically continuous deposit on keratinous materials. The composition may comprise an aqueous phase and the additional polymer may be present in this aqueous phase. In this case it will preferably be a polymer in dispersion or an amphiphilic or associative polymer.

The term "polymer in dispersion" means polymers that are not soluble in water present in the form of particles of variable size. The polymer may or may not be cross-linked. The mean particle size is typically in the range 25 to 500 nm, preferably in the range 50 to 200 nm. The following polymers in aqueous dispersion may be used: Ultrasol 2075 from Ganz Chemical, Daitosol 5000 AD from Daito Kasei, Avalure UR 450 from Noveon, DYNAMX from National Starch, Syntran 5760 from Interpolymer, Acusol OP 301 from Rohm&Haas, and Neocryl A 1090 from Avecia.

Acrylic dispersions sold under the trade names Neocryl XK-90®, Neocryl A-1070°, Neocryl A-1090®, Neocryl BT-62®, Neocryl A-1079® and Neocryl A-523® by the supplier AVECIA-NEORESINS, Dow Latex 432® by the supplier DOW CHEMICAL, Daitosol 5000 AD® or Daitosol 5000 SJ® by the supplier DAITO KASEY KOGYO; Syntran 5760® by the supplier Interpolymer, Soltex OPT by the supplier ROHM & HAAS, aqueous dispersions of acrylic or styrene/acrylic polymers sold under the trade name JON-CRYL® by the supplier JOHNSON POLYMER or aqueous dispersions of polyurethane sold under the trade names Neorez R-981® and Neorez R-974® by the supplier AVECIA-NEORESINS, Avalure UR-405®, Avalure UR-410®, Avalure UR-425®, Avalure UR-450®, Sancure 875®, Sancure 861®, Sancure 878® and Sancure 2060® by the supplier GOODRICH, Impranil 85® by the supplier BAYER, Aquamere H-1511® by the supplier HYDROMER; sulfopolyesters sold under the trade mark Eastman AQ® by the supplier Eastman Chemical Products, vinyl dispersions such as Mexomere PAM® from the supplier CHIMEX and mixtures thereof, are other examples of aqueous dispersions of hydrodispersible film-forming polymers.

The term "amphiphilic or associative polymers" means polymers comprising one or more hydrophilic portions that renders them partially soluble in water and one or more hydrophobic portions via which the polymers associate together or interact. The following associative polymers may be used: Nuvis FX1100 from Elementis, Aculyn 22, Aculyn 44, Aculyn 46 from Rohm&Haas, Viscophobe DB 1000 from Amerchol. Diblock copolymers constituted by a hydrophilic block (polyacrylate, polyethylene glycol) and a hydrophobic block (polystyrene, polysiloxane, may also be used.

The composition may comprise an oily phase and the film-forming polymer may be present in this oily phase. The polymer may thus be in dispersion or in solution.

Examples of non-aqueous dispersions of lipodispersible film-forming polymer in the form of non-aqueous dispersions of particles of polymer in one or more silicone and/or hydrocarbon oils that may be surface stabilized by at least one stabilizing agent, in particular a block, graft or random polymer, that may be cited are acrylic dispersions in isododecane such as Mexomere PAP® from the supplier CHIMEX, dispersions of particles of an ethylenic graft polymer, preferably acrylic, in a liquid fatty phase, the ethylenic polymer advantageously being dispersed in the absence of an additional stabilizer at the surface of the particles such as that described in particular in document WO 04/055081.

Examples of film-forming polymers that can be used in the composition of the present invention that may be cited are synthetic polymers of the radical or polycondensate type, polymers of natural origin and mixtures thereof.

The term "radical film-forming polymer" means a polymer obtained by polymerizing monomers with an unsaturated bond, in particular ethylenic, each monomer being capable of homopolymerizing (in contrast to polycondensates).

The radical type film-forming polymers may in particular be polymers or copolymers, or vinyls, in particular acrylic polymers.

The vinylic film-forming polymers may result from the polymerization of monomers with an ethylenically unsaturated bond having at least one acid group and/or esters of these acid monomers and/or amides of said acid monomers.

Examples of monomers carrying an acid group that may be used are $\alpha,\beta$-ethylenically unsaturated carboxylic acids such as acrylic acid, methacrylic acid, crotonic acid, maleic acid or itaconic acid. Preferably, (meth)acrylic acid and crotonic acid, more preferably (meth)acrylic acid, is used.

Advantageously, the esters of acid monomers are selected from esters of (meth)acrylic acid (also termed (meth)acrylates), in particular alkyl(meth)acrylates, in particular $C_1$-$C_{30}$ alkyl, preferably $C_1$-$C_{20}$ alkyl, aryl(meth)acrylates, in particular $C_6$-$C_{10}$ aryl, and hydroxyalkyl(meth)acrylates, in particular $C_2$-$C_6$ hydroxyalkyl.

The film-forming polymer may be selected from block or random polymers and/or copolymers, in particular comprising polyurethanes, polyacrylics, silicones, fluorinated polymers, butyl gums, ethylene copolymers, natural gums and polyvinyl alcohols, and mixtures thereof.

The vinyl film-forming polymers may also result from homopolymerization or copolymerization of monomers selected from vinyl esters and styrene monomers.

Examples of vinyl esters that may be cited are vinyl acetate, vinyl neodecanoate, vinyl pivalate, vinyl benzoate and vinyl t-butyl benzoate.

Styrene monomers that may be cited are styrene and alpha-methyl styrene.

Film-forming polycondensates that may be cited are polyurethanes, polyesters, polyester amides, polyamides, epoxyesters resins and polyureas.

The polyurethanes may be selected from anionic, cationic, non-ionic and amphoteric polyurethanes, polyurethane-acrylics, poly-urethane-polyvinylpyrrolidones, polyester-polyurethanes, polyether-polyurethanes, polyureas, poly-urea-polyurethanes, and mixtures thereof.

In known manner, the polyesters may be obtained by polycondensation of dicarboxylic acids with polyols, in particular diols.

In one example of a composition of the invention, the film-forming polymer may be a polymer dissolved in a liquid fatty phase comprising oils or organic solvents (the film-forming portion is then said to be a liposoluble polymer). Preferably, the liquid fatty phase comprises a volatile oil, optionally mixed with a non-volatile oil.

Examples of liposoluble polymers that may be cited are vinyl ester copolymers (the vinyl group being bonded directly to the oxygen atom of the ester group and the vinyl ester having a saturated, linear or branched hydrocarbon radical containing 1 to 19 carbon atoms bonded to the carbonyl of the ester group) and at least one other monomer which may be a vinyl ester (different from the vinyl ester already present), an $\alpha$-olefin (containing 8 to 28 carbon atoms), an alkyl vinyl ether (the alkyl group of which contains 2 to 18 carbon atoms), or an allyl or methallyl ester (containing a saturated, linear or branched hydrocarbon radical containing 1 to 19 carbon atoms, bonded to the carbonyl of the ester group).

These copolymers may be cross-linked by means of cross-linking agents that may be either of the vinyl type, or of the allyl or methallyl type, such as tetraallyloxyethane, divinylbenzene, divinyl octanedioate, divinyl dodecanedioate, or divinyl octadecanedioate.

Examples of liposoluble film-forming polymers that may be cited are copolymers of vinyl ester and at least one other monomer that may be a vinyl ester, in particular vinyl neodecanoate, vinyl benzoate and vinyl t-butyl benzoate, an α-olefin, an alkylvinylether, or an allyl or methallyl ester.

Examples of liposoluble film-forming polymers that may also be cited are liposoluble copolymers, in particular those resulting from the copolymerization of vinyl esters containing 9 to 22 carbon atoms or alkyl acrylates or methacrylates, alkyl radicals containing 10 to 20 carbon atoms.

Such liposoluble copolymers may be selected from copolymers of vinyl polystearate, vinyl polystearate crosslinked using divinylbenzene, diallylether or diallyl phthalate, copolymers stearyl poly(meth)acrylate, vinyl polylaurate, lauryl poly(meth)acrylate; these poly(meth)acrylates may be cross-linked with the aid of ethylene glycol dimethacrylate or tetraethylene glycol.

The liposoluble copolymers defined above are known and in particular have been described in application FR-A-2 232 303; they may have a mass average molecular weight of 2 000 to 500 000, preferably 4 000 to 200 000.

Examples of liposoluble film-forming polymers that may be used in the invention that may also be cited are polyalkylenes and especially copolymers of $C_2$-$C_{20}$ alkenes such as polybutene, and alkylcelluloses with a linear or branched, saturated or unsaturated $C_1$ to $C_8$ alkyl radical such as ethylcellulose or propylcellulose.

The composition of the invention may comprise a plasticizing agent favoring the formation of a film with the film-forming polymer. Said plasticizing agent may be selected from any compound known to the skilled person to be capable of having the desired function.

Other Polymers
Silicone Resins

The compositions of the invention may also comprise a silicone resin.

More generally, the term "resin" means a compound the structure of which is three-dimensional, "Silicone resins" are also known as "silicon-containing resins" or "siloxane resins". Thus, in the context of the present invention, a polydimethylsiloxane is not a silicone resin.

The nomenclature for silicone resins (also known as silicon-containing resins or siloxane resins) is known as "MDTQ", the resin being described as a function of the various monomeric siloxane units it includes, each of the letters "MDTQ" characterizing one type of unit.

The letter "M" represents the monofunctional unit with formula $R1R2R3SiO_{1/2}$, the silicon atom being bonded to a single oxygen atom in the polymer comprising this unit.

The letter "D" signifies a difunctional $R1R2SiO_{2/2}$ unit wherein the silicon atom is bonded to two oxygen atoms The letter "T" represents a trifunctional unit with formula $R1SiO_{3/2}$.

Such resins have, for example, been described in the "Encyclopedia of Polymer Science and Engineering, vol. 15, John and Wiley and Sons, New York, (1989), p. 265-270, and U.S. Pat. No. 2,676,182, U.S. Pat. No. 3,627,851, U.S. Pat. No. 3,772,247, U.S. Pat. No. 5,248,739 or U.S. Pat. No. 5,082,706, U.S. Pat. No. 5,319,040, U.S. Pat. No. 5,302,685 and U.S. Pat. No. 4,935,484.

In the motifs M, D, T defined above, R, namely R1, R2 and R3, represents a hydrocarbon radical (especially alkyl) containing 1 to 10 carbon atoms, a phenyl group, a phenylalkyl group or a hydroxyl group.

Finally, the letter "Q" signifies a tetrafunctional unit $SiO_{4/2}$ wherein the silicon atom is bonded to four oxygen atoms which are in turn bonded to the remainder of the polymer.

Various silicone resins with different properties may be obtained from these various units, the properties of these polymers varying as a function of the type of monomers (or units), the nature and number of the radical R, the length of the polymeric chain, the degree of branching and the size of the pendant chains.

Examples of silicone resins that could be used in the compositions of the invention that may, for example be used are silicone resins of the MQ type, T type or MQT type.

MQ Resins:

Examples of MQ type silicone resins that may be cited are alkylsiloxy silicates with formula $[(R1)_3SiO_{1/2}]_x(SiO_{4/2})_y$ (MQ units) wherein x and y are whole numbers ranging from 50 to 80, and such that the group R1 represents a radical as defined above, and is preferably an alkyl group containing 1 to 8 carbon atoms, or a hydroxyl group, preferably a methyl group;

examples of solid MQ type silicone resins of the trimethylsiloxysilicate type that may be cited are those sold with reference SR1000 by the supplier General Electric, with reference TMS 803 by the supplier Wacker, under the name "KF-7312J" by the supplier Shin-Etsu, "DC 749" and "DC 593" by the supplier Dow Corning;

examples of silicone resins comprising MQ type siloxysilicate motifs that may also be cited are phenylalkylsiloxysilicate resins such as phenylpropyldimethylsiloxysilicate (Silshine 151 sold by the supplier General Electric). The preparation of such resins is described in particular in U.S. Pat. No. 5,817,302.

T Resins:

Examples of type T silicone resins that may be cited are polysilsesquioxanes with formula $(RSiO_{3/2})_x$ (T units) wherein x is greater than 100 and such that the group R is an alkyl group containing 1 to 10 carbon atoms; said polysilsesquioxanes may also comprise terminal Si—OH groups.

Preferably, polymethylsilsesquioxane resins are used wherein R represents a methyl group such as, for example, those sold:

by the supplier Wacker with reference Resin MK such as Belsil PMS MK: polymer comprising $CH_3SiO_{3/2}$ repeat units (T units), possibly also comprising up to 1% by weight of $(CH_3)_2SiO_{2/2}$ units (D units) and having a mass average molecular weight of approximately 10000 g/mol; or by the supplier SHIN-ETSU with references KR-220L; these are compounds with T units with formula $CH_3SiO_{3/2}$ and have terminal Si—OH (silanol) groups, with reference KR-242A which comprise 98% of T units and 2% of dimethyl D units and have terminal Si—OH groups, or with reference KR-251 comprising 88% of T units and 12% of dimethyl D units and have terminal Si—OH groups.

MQT Resins:

Particular known examples of resins comprising MQT units are those cited in the document U.S. Pat. No. 5,110,890.

A preferred form of MQT type resins are MQT-propyl resins (also known as MQTPr). Such resins that can be used in the compositions of the invention are in particular those described and prepared in application WO 2005/075542, the contents of which are herewith incorporated by reference.

The MQ-T-propyl resin preferably comprises the units:
(i) $(R1_3SiO_{1/2})_a$;
(ii) $(R2_2SiO_{2/2})_b$;

(iii) $(R3SiO_{3/2})_c$; and
(iv) $(SiO_{4/2})_d$
with
R1, R2 and R3 independently representing a hydrocarbon radical (especially alkyl) containing 1 to 10 carbon atoms, a phenyl group, a phenylalkyl group or a hydroxyl group and preferably an alkyl radical containing 1 to 8 carbon atoms or a phenyl group;

a, b, c and d being molar fractions;
a being in the range 0.05 to 0.5;
b being in the range zero to 0.3;
c being greater than zero;
d being in the range 0.05 to 0.6;
a+b+c+d=1,
provided that more than 40 mole % of the R3 groups of the siloxane resin are propyl groups.

Preferably, the siloxane resin comprises the following units:
(i) $(R1_3SiO_{1/2})_a$;
(iii) $(R3SiO_{3/2})_c$; and
(iv) $(SiO_{4/2})_d$
with
R1 and R3 independently representing an alkyl group containing 1 to S carbon atoms, R1 preferably being a methyl group and R3 preferably being a propyl group;

a being in the range 0.05 to 0.5, preferably in the range 0.15 to 0.4;
c being greater than zero, preferably in the range 0.15 to 0.4;
d being in the range 0.05 to 0.6, preferably in the range 0.2 to 0.6, or more preferably in the range 0.2 to 0.55;
a+b+c+d=1;
provided that more than 40 mole % of the R3 groups of the siloxane resin are propyl groups.

The siloxane resins that may be used in the invention may be obtained by a method comprising reacting:

A) a MQ resin comprising at least 80 mole % of $(R1_3SiO_{1/2})_a$ and $(SiO_{4/2})_d$ units;
R1 representing an alkyl group containing 1 to 8 carbon atoms, an aryl group, a carbinol group or an amino group;
a and d being more than zero;
the ratio aid being in the range 0.5 to 1.5;
and
B) a propyl T resin comprising at least 80 mole % of $(R3SiO_{3/2})_c$ units;
R3 representing an alkyl group containing 1 to 8 carbon atoms, an aryl group, a carbinol group or an amino group;
c being greater than zero,
provided that least 40 mole % of the R3 groups are propyl groups;
where the A/B weight ratio is in the range 95:5 to 15:85; preferably the A/B weight ratio is 30:70.

Advantageously, the A/B weight ratio is in the range 95:5 to 15:85. Preferably, the ratio A/B is 70:30 or less. These preferred ratios have proved to be comfortable when applied.

Preferably, when it is present, the siloxane resin is present in the composition in a total dry matter content for the resin of 3% to 40% by weight with respect to the total weight of the composition, preferably 4% to 30% by weight, and more preferably 4% to 25% by weight.

It should be understood that the quantity of these auxiliary compounds may be adjusted by the skilled person so as not to be detrimental to sired effect in the context of the present invention.

Semi-Crystalline Polymer

The composition in accordance with the invention may also advantageously comprise at least one semi-crystalline polymer with an organic structure having a temperature of melting of 30° C. or more.

Preferably, the total quantity of semi-crystalline polymer(s) represents 0.1% to 45% of the total composition weight, preferably 0.5% to 40%, for example 1% to 35% by weight, and more preferably 1% to 20%, or more preferably 3% to 30%, 5% to 30%, or even 15% to 30%. Preferably, it represents 2% to 10% of the composition weight.

The term "polymers" as used in the context of the invention means compounds comprising at least 2 repeat motifs, preferably at least 3 repeat motifs and more specifically at least 10 repeat motifs.

The term "semi-crystalline polymer" as used in the context of the invention means polymers comprising a crystallizable portion and an amorphous portion and having a first order reversible phase change temperature, in particular the temperature of melting (solid-liquid transition). The crystallizable portion is either a side chain (or pendant chain) or a sequence in the backbone.

When the crystallizable portion of the semi-crystalline polymer is a sequence of the polymeric backbone, this crystallizable sequence has a different chemical nature to that of the amorphous sequences; the semi-crystalline polymer in this case is a sequenced copolymer, for example of the diblock, triblock or multiblock type. When the crystallizable portion is a pendant chain on the backbone, the semi-crystalline polymer may be a homopolymer or a copolymer.

The term "organic compound" or "with an organic structure" means compounds containing carbon atoms and hydrogen atoms and possibly heteroatoms such as S, O, N, P, alone or in combination.

The temperature of melting of the semi-crystalline polymer is preferably less than 150° C.

The temperature of melting of the semi-crystalline polymer is preferably 30° C. or more and less than 100° C. More preferably, the temperature of melting of the semi-crystalline polymer is preferably 30° C. or more and less than 70° C.

The semi-crystalline polymer or polymers of the present invention are solids at ambient temperature (25° C.) and atmospheric pressure (760 mm Hg), wherein the temperature of melting is 30° C. or more. The values for the melting point correspond to the melting point measured using a differential scanning calorimeter (DSC) such as the calorimeter sold under the trade name DSC 30 by the supplier METTLER, with a temperature rise of 5° C. or 10° C. per minute. (The melting point under consideration is the point corresponding to the temperature of the most endothermic peak of the thermogram).

The semi-crystalline polymer or polymers of the invention preferably have a temperature of melting higher than the temperature of the keratinous support intended to receive said composition, in particular the skin or lips.

In accordance with the invention, the semi-crystalline polymers are advantageously soluble in the fatty phase, especially in a proportion of at least 1% by weight, at a temperature higher than their temperature of melting. Beyond the crystallizable chains or sequences, the polymer sequences are amorphous.

The term "crystallizable chain or sequence" as used in the context of the invention means a chain or sequence which, if it was alone, would change from the amorphous state to the crystalline state in a reversible manner depending on whether it was above or below the temperature of melting. A "chain" in the context of the invention is a group of atoms which are pendant or lateral with respect to the polymer backbone. A sequence is a group of atoms belonging to the backbone; the group constitutes one of the repeat motifs of the polymer.

Preferably, the polymeric backbone of the semi-crystalline polymers is soluble in the fatty phase at a temperature above their temperature of melting.

Preferably, the crystallizable sequences or chains of semi-crystalline polymers represent at least 30% of the total weight of each polymer and more preferably at least 40%. The semi-crystalline polymers with crystallizable side chains are homo- or copolymers. The semi-crystalline polymers of the invention with crystallizable sequences are sequenced or multi-sequenced copolymers. They may be obtained by polymerizing monomers with reactive double (or ethylenic) bonds or by polycondensation. When the polymers of the invention are polymers with crystallizable side chains, these latter are advantageously in the random or statistical form.

Preferably, the semi-crystalline polymers of the invention are of synthetic origin.

In a preferred embodiment, the semi-crystalline polymer is selected from:
 homopolymers and copolymers comprising motifs resulting from the polymerization of one or more monomers carrying hydrophobic crystallizable side chain(s);
 polymers carrying at least one crystallizable sequence in their backbone;
 aliphatic or aromatic or aliphatic/aromatic polyester type polycondensates;
 copolymers of ethylene and propylene prepared by metallocene catalysis.

In particular, the semi-crystalline polymers for use in the invention may be selected from:
 sequenced copolymers of polyolefins with a controlled crystallization; the monomers thereof have been described in EP-A-0 951 897;
 polycondensates, in particular of the aliphatic or aromatic or aliphatic/aromatic polyester type;
 copolymers of ethylene and propylene prepared by metallocene catalysis;
 homo- or copolymers carrying at least one crystallizable side chain and homo- or copolymers carrying at least one crystallizable sequence in the backbone, such as those described in document U.S. Pat. No. 5,156,911;
 homo- or copolymers carrying at least one crystallizable side chain, in particular with fluorinated group(s), such as those described in document WO-A-01/19333;
 and mixtures thereof.

In the last two cases, the side chain or chains or crystallizable sequences are hydrophobic.

A) semi-crystalline polymers with crystallizable side chains.

Particular examples that may be cited are those defined in documents U.S. Pat. No. 5,156,911 and WO-A-01/19333.

They are homopolymers or copolymers comprising 50% to 100% by weight of motifs resulting from the polymerization of one or more monomers carrying a crystallizable hydrophobic side chain.

These homo- or copolymers are of any nature as long as they have the conditions indicated below, in particular the characteristic of being soluble or dispersible in the fatty phase by heating to above their temperature of melting MP. They may result:
 from the polymerization, especially radical, of one or more monomers with reactive double or ethylenic bond(s) as regards polymerization, namely a vinyl, (meth)acrylic or allyl group;

from polycondensation of one or more monomers carrying co-reactive groups (carboxylic or sulfonic acid, alcohol, amine or isocyanate), such as polyesters, polyurethanes, polyethers or polyureas.

a) In general, the crystallizable motifs (chains or sequences) of the semi-crystalline polymers of the invention derive from monomers with crystallizable chain(s) or sequence(s) used for the manufacture of semi-crystalline polymers. These polymers are in particular selected from homopolymers and copolymers resulting from the polymerization of at least one monomer with crystallizable chain(s) that may be represented by the formula X:

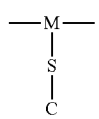

with M representing an atom of the polymeric backbone;
C representing a crystallizable group; and
S representing a spacer.

The crystallizable "—S—C" chains may be aliphatic or aromatic, possibly fluorinated or perfluorinated. "C" in particular represents a linear or branched or cyclic $(CH_2)_n$ group in which n is a whole number from 12 to 40. Preferably, "C" is a linear group. Preferably, "S" and "C" are different.

When the crystallizable chains are aliphatic hydrocarbon chains, they comprise hydrocarbon alkyl chains containing at least 12 carbon atoms and at most 40 carbon atoms, preferably at most 24 carbon atoms. In particular they are aliphatic chains or alkyl chains having at least 12 carbon atoms; preferably, they are $C_{14}$-$C_{24}$ alkyl chains, preferably $C_{16}$-$C_{22}$. When the alkyl chains are fluorinated or perfluorinated, they contain at least 11 carbon atoms wherein at least 6 carbon atoms are fluorinated.

Examples of semi-crystalline homopolymers or copolymers with crystallizable chain(s) that may be cited are those resulting from the polymerization of one or more of the following monomers: saturated alkyl(meth)acrylates with a $C_{14}$-$C_{24}$ alkyl group, perfluoroalkyl(meth)acrylates with a $C_{11}$-$C_{15}$ perfluoroalkyl group, N-alkyl(meth)acrylamides having a $C_{14}$ to $C_{24}$ alkyl group with or without a fluorine atom, vinyl esters with alkyl or perfluoro(alkyl) chains having a $C_{14}$ to $C_{24}$ alkyl group (with at least 6 fluorine atoms for a perfluoroalkyl group), vinyl ethers with alkyl or perfluoro(alkyl) chains having a $C_{14}$ to $C_{24}$ alkyl group and at least 6 fluorine atoms per perfluoroalkyl chain, $C_{14}$ to $C_{24}$ alpha-olefins such as octadecene, for example, para-alkyl styrenes with an alkyl group containing 12 to 24 carbon atoms, and mixtures thereof.

When the polymers result from polycondensation, the crystallizable hydrocarbon and/or fluorinated chains as defined above are carried by a monomer which may be a diacid, a dial, a diamine or a diisocyanate.

When the polymers of the invention are copolymers, they additionally contain 0 to 50% of Y groups, namely a polar or non-polar monomer or a mixture of the two:

When Y is a polar monomer, it is either a monomer carrying polyoxyalkylene groups (especially oxyethylenated and/or oxypropylenated), a hydroxyalkyl(meth)acrylate such as hydroxyethyl acrylate, (meth)acrylamide, a N-alkyl(meth)acrylamide, a N,N-dialkyl(meth)acrylamide such as, for example, N,N-diisopropylacrylamide or N-vinylpyrrolidone (NVP), N-vinyl caprolactam, a monomer carrying at least one carboxylic acid group such as (meth)acrylic, crotonic, itaconic, maleic, or fumaric acid, or carrying a carboxylic acid anhydride group such as maleic anhydride, and mixtures thereof.

When Y is a non-polar monomer, it may be an ester of the linear, branched or cyclic alkyl(meth)acrylate type, a vinyl ester, an alkyl vinyl ether, an alpha-olefin, styrene or styrene substituted with a $C_1$ to $C_{10}$ alkyl group such as α-methylstyrene, or a macromonomer of the polyorganosiloxane type with a vinylic unsaturated bond.

The term "alkyl" as used in the context in the context of the invention means a saturated group, in particular $C_8$ to $C_{24}$, unless otherwise specified.

Preferably, the semi-crystalline polymers with a crystallizable side chain are homopolymers of alkyl(meth)acrylate or alkyl(meth)acrylamide with an alkyl group as defined above, and in particular $C_{14}$-$C_{24}$, copolymers of said monomers with a hydrophilic monomer, preferably with a nature that is different from the (meth)acrylic acid, such as N-vinylpyrrolidone or hydroxyethyl(meth)acrylate, and mixtures thereof.

Advantageously, the semi-crystalline polymer or polymers with a crystallizable side chain have a mass average molecular mass MW of 5 000 to 1 000 000, preferably 10 000 to 800 000, preferably 15 000 to 500 000, more preferably 100 000 to 200 000.

Particular examples of semi-crystalline polymers that may be used in the composition of the invention that may be cited are Intelimer® products from the supplier Landec described in the brochure "Intelimer® polymers", Landec IP22 (Version 4-97). These polymers are in the solid form at ambient temperature (25° C.). They carry crystallizable side chains and have the formula X given above.

As an example, the product Jntelimer® IPA 13-1 from the supplier Landec is selected; it is a stearyl polyacrylate with a molecular weight of approximately 145 000 and a temperature of melting of 49° C.

The semi-crystalline polymers may in particular be those described in Examples 3, 4, 5, 7, 9 of U.S. Pat. No. 5,156,911 and more particularly of the copolymerization:

of acrylic acid, hexadecylacrylate and isodecylacrylate in a ratio 1/16/3;

acrylic acid and pentadecylacrylate in a ratio 1/19;

acrylic acid, hexadecylacrylate, ethylacrylate in a ratio 2.5/76.5/20;

acrylic acid, hexadecylacrylate and methylacrylate in a ratio 5/85/10;

acrylic acid, polyoctadecylmethacrylate in a ratio 2.5/97.5.

It is also possible to use the polymer "Structure O" from National Starch as described in the document U.S. Pat. No. 5,736,125, with a temperature of melting of 44° C.

The semi-crystalline polymers may in particular be semi-crystalline polymers with crystallizable pendant chains comprising fluorinated groups as described in Examples 1, 4, 6, 7 and 8 of document WO-A-01/19333.

It is also possible to use the semi-crystalline polymers obtained by the copolymerization of stearyl acrylate and acrylic acid or NVP as described in the document U.S. Pat. No. 5,519,063 or EP-A-0 550 745.

It is also possible to use the semi-crystalline polymers obtained by the copolymerization of behenyl acrylate and acrylic acid or NVP, as described in documents U.S. Pat. No. 5,519,063 and EP-A-055 0745 and more particularly those described in Examples 3 and 4 below for the preparation of the polymer.

B) Polymers carrying at least one crystallizable sequence in the backbone.

These are polymers that are soluble or dispersible in the fatty phase by heating to above their melting point MP. In particular, these polymers are sequenced copolymers constituted by at least two sequences with different chemical natures one of which is crystallizable.

The polymer carrying at least one crystallizable sequence in its backbone may be selected from sequenced copolymers of olefin or cyclo-olefin with a crystallizable chain such as those derived from the sequenced polymerization of:

cyclobutene, cyclohexene, cyclooctene, norbornene (i.e. bicyclo(2,2,1)heptene-2), 5-methylnorbornene, 5-ethylnorbornene, 5,6-dimethylnorbornene, 5,5,6-trimethyl norbornene, 5-ethylidene-norbornene, 5-phenyl-norbonene, 5-benzylnorbornene, 5-vinyl norbornene, 1,4,5,8-dimethano-1,2,3,4,4a,5,8a-octahydronaphtalene, dicyclopentadiene or mixtures thereof, with ethylene, propylene, 1-butene, 3-methyl-1-butene, 1-hexene; 4-methyl-1-pentene, 1-octene, 1-decene, 1-eicosene or mixtures thereof;

and in particular copoly(ethylene/norbornene) blocks and (ethylene/propylene/ethylidene-norbornene) terpolymer blocks. It is also possible to use those resulting from the sequenced copolymerization of at least 2 $C_2$-$C_{16}$ α-olefins, preferably $C_2$-$C_{12}$, such as those cited above, and in particular sequenced bi-polymers of ethylene and 1-octene.

The polymer carrying at least one crystallizable sequence in the backbone may be selected from copolymers having at least one crystallizable sequence, the remainder of the copolymer being amorphous (at ambient temperature). These copolymers may also have two crystallizable sequences of different chemical natures.

Preferred copolymers are those which at ambient temperature have both a crystallizable sequence and a lipophilic amorphous sequence, distributed sequentially. Examples of polymers having one crystallizable sequence and one amorphous sequence that may be cited are as follows:

polyester type crystallizable sequences such as poly(alkylene terephthalate)s, or of the polyolefin type such as polyethylenes or poly propylenes;

amorphous and lipophilic sequences such as amorphous polyolefins or copoly(olefin)s such as poly(isobutylene), hydrogenated polybutadiene, or hydrogenated poly(isoprene).

Examples of such copolymers with a crystallizable sequence and with an amorphous sequence that may be cited are:

α) poly(ϵ-caprolactone)-b-poly(butadiene) sequenced copolymers, preferably used in the hydrogenated form, such as those described in the article D6 "Melting behavior of poly(-caprolactone)-block-polybutadiene copolymers" by S Nojima, Macromolecules, 32, 3727-3734 (1999);

β) hydrogenated sequenced or multi-sequenced poly(butyleneterephthalate)-b-poly(isoprene) copolymers cited in the article D7 "Study of morphological and mechanical properties of PP/PBT" by B Boutevin et al., Polymer Bulletin, 34, 117-123 (1995);

γ) the poly(ethylene)-b-copoly(ethylene/propylene) sequenced copolymers cited in the articles D8 "Morphology of semi-crystalline block copolymers of ethylene-(ethylene-alt-propylene)" by P Rangarajan et al., Macromolecules 26, 4640-4645 (1993) and D9 "Polymer aggregates with crystalline cores: the system poly(ethylene)-poly(ethylene-propylene)" P Richter et al., Macromolecules, 30, 1053-1068 (1997);

δ) the poly(ethylene)-b-poly(ethylethylene) sequenced copolymers cited in the general article D10 "Crystallization in block copolymers" by I W Hamley, Advances in Polymer Science, vol 148, 113-137 (1999).

C) Aliphatic or aromatic or aliphatic/aromatic polyester type polycondensates

The polyester polycondensates may be selected from aliphatic polyesters. Their molecular mass is preferably 200 or more and 10 000 or less, more preferably 300 or more and 5 000 or less, preferably 500 or more and 2 000 g/mol or less.

The polyester polycondensates are in particular selected from polycaprolactones. In particular, the polycaprolactones may be selected from homopolymers of ϵ-caprolactones. The homopolymerization may be initiated with a diol, especially a diol containing 2 to 10 carbon atoms, such as diethylene glycol, 1,4-butanediol, or neopentyl glycol.

Polycaprolactones may, for example, be used, especially those sold under the trade name CAPA® 240 (melting point 68° C. and molecular weight 4000), 223 (melting point 48° C. and molecular weight 2000), 222 (melting point 48° C. and molecular weight 2000), 217 (melting point 44° C. and molecular weight 1250), 2125 (melting point 45° C. and molecular weight 1250), 212 (melting point 45° C. and molecular weight 1000), 210 (melting point 38° C. and molecular weight 1000), 205 (melting point 39° C. and molecular weight 830) by the supplier SOLVAY, PCL-300, PCL-700 by the supplier UNION CARBIDE.

In particular, CAPA® 2125 may be used; its temperature of melting is in the range 35° C. to 45° C. and its mass average molecular mass is equal to 1250.

The semi-crystalline polymers of the composition of the invention may or may not be cross-linked as long as the degree of cross-linking does not compromise their being dissolved or dispersed in the fatty phase by heating above their temperature of melting. The cross-linking may thus be chemical cross-linking by reaction with a multi-functional monomer during polymerization. It may also be physical cross-linking that may then be due either to establishing hydrogen or dipole type bonds between groups carried by the polymer such as, for example, dipole interactions between carboxylate ionomers, these interactions being small in quantity and carried by the polymer backbone; or a phase separation between the crystallizable sequences and the amorphous sequences carried by the polymer.

Preferably, the semi-crystalline polymers of the composition of the invention are not cross-linked.

D) Copolymers of ethylene and propylene prepared by metallocene catalysis

The semi-crystalline polymer of the composition of the invention may also be a polymer obtained by metallocene catalysis, such as those described in patent US 2007/0031361 the contents of which are herewith incorporated by reference.

These polymers are copolymers of ethylene and propylene prepared by metallocene catalysis, i.e. by polymerization at low pressure and in the presence of a metallocene catalyst.

The mass average molecular mass (Mw) of these copolymers obtained by metallocene catalysis described in this document is 25 000 g/mol or less; as an example, it is from 2 000 to 22 000 g/mol, preferably 4 000 to 20 000 g/mol.

The mass average molecular mass (Mw) of these copolymers obtained by metallocene catalysis described in this document is preferably 15 000 g/mol or less; as an example, it is from 1 000 to 12 000 g/mol, preferably 2 000 to 10 000 g/mol.

The polydispersity index 1 of the polymer is equal to the ratio of the mass average molecular mass Mw over the number average molecular mass Mn.

Preferably, the polydispersity index of the copolymers is in the range 1.5 to 10, preferably in the range 1.5 to 5, preferably in the range 1.5 to 3 and more preferably in the range 2 to 2.5.

The copolymers may be obtained in known manner starting from ethylene and/or propylene monomers, for example by metallocene catalysis using the method described in the document EP 0 571 882 the contents of which are herewith incorporated by reference.

The copolymers of ethylene and propylene prepared by metallocene catalysis may be non-modified or "polar" modified, i.e. modified so that they exhibit polar groups. The polar modified copolymers may be prepared in known manner from non-modified homopolymers and copolymers such as those described above by oxidation with gases containing oxygen such as air or by grafting with polar monomers such as maleic acid or acrylic acid or derivatives of these acids. These two pathways mean that the polyolefins obtained by metallocene catalysis respectively described in documents EP 0 890 583 and U.S. Pat. No. 5,998,547 for example can be polar modified, the contents of these two documents being herewith incorporated by reference.

In accordance with the present invention, particularly preferred polar modified copolymers of ethylene and/or propylene prepared by metallocene catalysis are polymers modified so that they exhibit hydrophilic properties. Examples that may be cited are homopolymers or copolymers of ethylene and/or propylene modified by the presence of hydrophilic groups such as maleic anhydride, acrylate, methacrylate, polyvinylpyrrolidone (PVP), etc.

Homopolymers or copolymers of ethylene and/or propylene modified by the presence of hydrophilic groups such as maleic anhydride or acrylate are particularly preferred.

Examples that may be cited are:

polypropylene polymers modified with maleic anhydride (PPMA) sold by the supplier Clariant or polypropylene-ethylene-maleic anhydride copolymers, such as those sold by the supplier Clariant under the trade name LicoCare such as LicoCare PP207 LP3349, LicoCare CM401 LP3345, LicoCare CA301 LP 3346, or LicoCare CA302 LP 3347.

In the context of a composition for the lips, a polar modified polymer with a low degree of crystallinity is preferred, preferably with less than 40%.

Other Structuring Agents

The composition of the present invention may also comprise structuring agents other than the wax described above. The term "structuring agent" means a compound that is capable of increasing the viscosity of the composition into which it is incorporated. The structuring agent may in particular produce a composition that may have a texture varying from fluid to solid textures.

In this regard, the following may in particular be cited:

organophilic clays such as hectorites modified by a $C_{10}$ to $C_{22}$ ammonium chloride, such as hectorite modified by distearyl dimethyl ammonium chloride such as, for example, that sold under the trade name Bentone 38V® by the supplier ELEMENTIS;

pyrogenic silicas such as pyrogenic silicas that may optionally be hydrophobically treated at the surface, with a particle size of less than 1 μm. It is in fact possible to chemically modify the surface of the silica by chemical reaction generating a reduction in the number of silanol groups present on the silica surface. In particular, it is possible to substitute silanol groups with hydrophobic groups: a hydrophobic silica is thus obtained. The hydrophobic groups may be:

1. trimethylsiloxyl groups, which are in particular obtained by the treatment of pyrogenic silica in the presence of hexamethyldisilazane. Such treated silicas are denoted "Silica silylate" by the CTFA (8th edition, 2000). They are, for example, sold with references Aerosil R812® by the supplier DEGUSSA, and CAB-O-SIL TS-530® by the supplier CABOT;

2. dimethylsilyloxyl groups or polydimethylsiloxane groups, which are in particular obtained by the treatment of pyrogenic silica in the presence of polydimethylsiloxane or dimethyldichlorosilane. Such treated silicas are denoted "Silica dimethyl silylate" by the CTFA (8th edition, 2000). They are, for example, sold with references Aerosil R972®, and Aerosil R974® by the supplier DEGUSSA and CAB-O-SIL TS-610® and CAB-O-SIL TS-720® by the supplier CABOT;

alkylated guar gums (with a $C_1$-$C_6$ alkyl group), such as those described in EP-A-0 708 114, or for example cellulose derivatives such as ethylcellulose, as sold under the trade name Ethocel® by the supplier DOW CHEMICAL;

hydrocarbon sequenced copolymers generally termed block copolymers, preferably a sequenced copolymer that is soluble in or dispersible in a liquid fatty phase;

The hydrocarbon block copolymer may in particular be a diblock, triblock, multiblock, radial, star copolymer or a mixture thereof.

Such hydrocarbon block copolymers are described in application US-A-2002/005562 and in U.S. Pat. No. 5,221,534.

Examples of diblock copolymers, preferably hydrogenated, that may be cited are styrene-ethylene-propylene copolymers, styrene-ethylene/butadiene copolymers, and styrene-ethylene/butylene copolymers. The diblock polymers are in particular sold under the trade name Kraton® G1701E by the supplier Kraton Polymers;

Examples of triblock copolymers, preferably hydrogenated, that may be cited are styrene-ethylene/propylene-styrene copolymers, styrene-ethylene/butadiene-styrene copolymers, styrene-ethylene/butylene-styrene copolymers, styrene-isoprene-styrene copolymers, and styrene-butadiene-styrene copolymers. Triblock polymers are in particular sold under the trade names Kraton® G1650, Kraton® G1652, Kraton® D1101, Kraton® D1102, and Kraton® D1160 by the supplier Kraton Polymers;

and mixtures thereof.

Other structuring agents may be included in the composition of the invention in an amount in the range 0.5% to 20% by weight, in particular in the range 0.5% to 10% by weight, with respect to the total composition weight.

Colorizing Substances

The compositions of the invention may advantageously contain a colorizing agent that may be selected from hydrosoluble or liposoluble dyes, pigments, nacres and mixtures thereof.

The composition of the invention may also comprise one or more colorizing substances selected from hydrosoluble dyes and powdered colorizing substances such as pigments, nacres, and flakes that are well known to the skilled person. The colorizing substances may be present in the composition in an amount of 0.01% to 50% by weight with respect to the weight of the composition, preferably 0.01% to 30% by weight and in particular 0.05% to 25% by weight with respect to the total composition weight.

The term "pigments" should be understood to mean white or colored, mineral or organic particles that are insoluble in an aqueous solution, intended to colorize and/or opacify the resulting film.

The pigments may be present in an amount of 0.01% to 20% by weight, especially 0.01% to 15% by weight, and in particular 0.02% to 10% by weight with respect to the total cosmetic composition weight.

Examples of mineral pigments that could be used in the invention that may be cited are oxides of titanium, zirconium or cerium as well as oxides of zinc, iron or chromium, ferric blue, manganese violet, ultramarine blue and chromium hydrate.

They may also be pigments with a structure that may, for example, be of the sericite/brown iron oxide/titanium dioxide/silica type. Such a pigment is sold, for example, with reference COVERLEAF NS or JS by the supplier CHEMICALS AND CATALYSTS.

The colorizing substances may also comprise a pigment having a structure that may, for example, be of the silica microsphere type containing iron oxide. An example of a pigment having this structure is that sold by the supplier MIYOSHI with reference PC BALL PC-LL-100 P, this pigment being constituted by silica microspheres containing yellow iron oxide.

Examples of organic pigments that may be used in the invention that may be cited are carbon black, D&C type pigments, lakes based on cochineal carmine, barium, strontium, calcium, aluminum or the diketo pyrrolopyrroles (DPP) described in the documents EP-A-0 542 669, EP-A-0 787 730, EP-A-0 787 731 and WO-A-96/08537.

The term "nacres" should be understood to mean colored particles of any shape, iridescent or otherwise, in particular produced in the shells of certain mollusks or which are synthesized and which produce a color effect by optical interference.

The nacres may be selected from nacreous pigments such as mica titanium coated with iron oxide, mica titanium coated with bismuth oxychloride, mica titanium coated with chromium oxide, mica titanium coated with an organic colorizing agent as well as nacreous pigments based on bismuth oxychloride. They may also be particles of mica the surfaces of which have superimposed thereon at least two successive layers of metallic oxides and/or organic colorizing substances.

Further examples of nacres that may be cited are natural mica coated with titanium oxide, iron oxide, natural pigment or bismuth oxychloride.

Examples of nacres that are commercially available that may be cited are TIMICA, FLAMENCO and DUOCHROME (mica-based) nacres sold by the supplier ENGELHARD, TIMIRON nacres sold by the supplier MERCK, PRESTIGE mica-based nacres sold by the supplier ECKART and SUNSHINE synthetic mica-based nacres sold by the supplier SUN CHEMICAL.

More particularly, the nacres may have a color or a yellow, pink, red, bronze, orangey, brown, gold and/or coppery glint.

Illustrative examples of nacres that may be used in the context of the present invention that may in particular be cited are gold colored nacres especially those sold by the supplier ENGELHARD under the trade name Brillant gold 212G (Timica), Gold 222C (Cloisonne), Sparkle gold (Timica), Gold 4504 (Chromalite) and Monarch gold 233X (Cloisonne); bronze nacres, in particular sold by the supplier MERCK under the trade name Bronze fine (17384) (Colorona) and Bronze (17353) (Colorona) and by the supplier ENGELHARD under the trade name Super bronze (Cloisonne); orange nacres in particular sold by the supplier ENGELHARD under the trade name Orange 363C (Cloisonne) and Orange MCR 101 (Cosmica) and by the supplier MERCK under the trade name Passion orange (Colorona)

and Matte orange (17449) (Microna); nac res with a brown hue in particular sold by the supplier ENGELHARD under the trade name Nu-antique copper 340XB (Cloisonne) and Brown CL4509 (Chromalite); nacres with a copper glint in particular sold by the supplier ENGELHARD under the trade name Copper 340A (Timica); nacres with a red glint in particular sold by the supplier MERCK under the trade name Sienna fine (17386) (Colorona); nacres with a yellow glint in particular sold by the supplier ENGELHARD under the trade name Yellow (4502) (Chromalite); nacres with a red hue and a gold glint in particular sold by the supplier ENGELHARD under the trade name Sunstone G012 (Gemtone); pink nacres in particular sold by the supplier ENGELHARD under the trade name Tan opale G005 (Gemtone); black nacres with a gold glint sold by the supplier ENGELHARD under the trade name Nu antique bronze 240 AB (Timica), blue nacres in particular sold by the supplier MERCK under the trade name Matte blue (17433) (Microna), white nacres with a silvery glint in particular sold by the supplier MERCK under the trade name Xirona Silver, and orangey-pink green-gold nacres in particular sold by the supplier MERCK under the trade name Indian summer (Xirona), and mixtures thereof.

The term "dyes" should be understood to mean generally organic compounds that are soluble in fats such as oils or in a hydroalcoholic phase.

The liposoluble dyes may be selected from Sudan red, DC Red 17, DC green 6, β-carotene, Sudan brown, DC Yellow 11, DC Violet 2, DC orange 5, and quinolein yellow. Examples of hydrosoluble dyes are beetroot juice and methylene blue.

The cosmetic composition of the invention may also contain at least one material with a specific optical effect.

This effect is different from a simple conventional hue effect, i.e. unified and stabilized such as that produced by the customary colorizing substances such as monochromatic pigments. In the context of the invention, "stabilized" means free of a color variability effect with the angle of observation or in response to a temperature change.

As an example, this material may be selected from particles with a metallic glint, goniochromatic colorizing agents, diffracting pigments, thermochromic agents, optical brighteners, as well as fibers, in particular interference fibers. Clearly, these various materials may be combined in order to simultaneously produce two effects.

Particular examples of particles with a metallic glint that may be used in the invention are selected from:
 particles of at least one metal and/or at least one metallic derivative;
 particles comprising a substrate, organic or mineral, of one substance or a multimaterial, at least partially coated with at least one layer with a metallic glint comprising at least one metal and/or at least one metallic derivative; and
 mixtures of said particles.

Examples of metals that may be present in said particles that may be cited are Ag, Au, Cu, Al, Ni, Sn, Mg, Cr, Mo, Ti, Zr, Pt, Va, Rb, W, Zn, Ge, Te, Se and mixtures or alloys thereof. Ag, Au, Cu, Al, Zn, Ni, Mo, Cr and mixtures thereof or alloys (for example bronzes and brasses) are preferred metals.

The term "metallic derivatives" means compounds derived from metals, in particular oxides, fluorides, chlorides and sulfides.

Illustrative examples of said particles that may be cited are particles of aluminum such as those sold under the trade names STARBRITE 1200 EAC® by the supplier SIBERLINE and METALURE® by the supplier ECKART.

It is also possible to cite metallic powders of copper or mixtures of alloys such as references 2844 sold by the supplier RADIUM BRONZE, metallic pigments such as aluminum or bronze, such as those sold under the trade names ROTOSAFE 700 from the supplier ECKART, aluminum particles coated with silica sold under the trade name VISIONAIRE BRIGHT SILVER from the supplier ECKART and particles of metal alloys such as bronze powders (copper and zinc alloy) coated with silica sold under the trade name Visionaire Bright Natural Gold from the supplier Eckart.

They may also be particles comprising a glass substrate, such as those sold by the supplier NIPPON SHEET GLASS under the trade names MICROGLASS METASHINE.

The goniochromatic colorizing agent may, for example, be selected from multilayer interference structures and liquid crystal colorizing agents.

Examples of symmetrical multilayer interference structures that may be used in compositions produced in accordance with the invention are the following structures:

$Al/SiO_2/Al/SiO_2/Al$, pigments having this structure being sold by the supplier DUPONT DE NEMOURS; $Cr/MgF_2/Al/MgF_2/Cr$, pigments having this structure being sold under the trade name CHROMAFLAIR by the supplier FLEX; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the trade name SICOPEARL by the supplier BASF; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the trade name XIRONA by the supplier MERCK (Darmstadt). By way of example, these pigments may be pigments with a silica/titanium oxide/tin oxide structure sold under the trade name XIRONA MAGIC by the supplier MERCK, pigments with a silica/brown iron oxide structure sold under the trade name XIRONA INDIAN SUMMER by the supplier MERCK and pigments with a silica/titanium oxide/mica/tin oxide structure sold under the trade name XIRONA CARIBBEAN BLUE by the supplier MERCK. It is also possible to cite INFINITE COLORS pigments from the supplier SHISEIDO. Different effects are obtained as a function of the thickness and nature of the various layers. Thus, the $Fe_2O_3/SiO_2/Al/SiO_2/Fe_2O_3$ structure changes from green-gold to gray-red for $SiO_2$ layers of 320 to 350 nm; from red to golden for layers of $SiO_2$ of 380 to 400 nm; from violet to green for layers of $SiO_2$ of 410 to 420 nm; and from copper to red for layers of $SiO_2$ from 430 to 440 nm.

Examples of pigments with a polymeric multilayer structure that may be cited are those sold by the supplier 3M under the trade name COLOR GLITTER.

Examples of goniochromatic particles with liquid crystals that may be used, for example, are those sold by the supplier CHENIX as well as those sold under the trade name HELICONE® HC by the supplier WACKER.

Filler

A composition in accordance with the invention may comprise a filler, especially in a total quantity of 0.01% to 30%, in particular 0.01% to 20% by weight, for example from 0.1% to 15% or from 0.5% to 10% by weight with respect to the total composition weight.

The term "filler" as used in the context of the present invention means particles of any shape, colorless or white, mineral or synthesized, insoluble in the composition medium irrespective of the temperature at which the composition is manufactured. These fillers act in particular to modify the rheology or texture of the composition.

The fillers may be mineral or organic of any shape, wafers, spherical or oblong, irrespective of the crystal form (for example sheet, cubic, hexagonal, orthorhombic, etc.). It is possible to cite talc, mica, silica, kaolin, powders of polyamide (Nylon®) (Orgasol® from Atochem), of poly-β-alanine and of polyethylene, powders of tetrafluoroethylene polymers (Teflon®), lauroyl-lysine, starch, boron nitride, hollow polymeric microspheres such as those formed from polyvinylidene chloride/acrylonitrile such as Expancel® (Nobel Industrie), acrylic acid copolymers (Polytrap® from the supplier Dow Corning) and silicone resin microbeads (Tospearls® from Toshiba, for example), elastomeric polyorganosiloxane particles, precipitated calcium carbonate, magnesium carbonate and bicarbonate, hydroxyapatite, hollow silica microspheres (Silica Beads® from Maprecos), glass or ceramic microcapsules, metallic soaps derived from organic carboxylic acids containing 8 to 22 carbon atoms, preferably 12 to 18 carbon atoms, for example zinc, magnesium or lithium stearate, zinc laurate, or magnesium myristate.

They may also be particles comprising a copolymer, said copolymer comprising trimethylol hexyllactone. In particular, they may be copolymers of hexamethylene di-isocyanate/trimethylol hexyllactone. Such particles are commercially available, for example under the trade name PLASTIC POWDER D-400® or PLASTIC POWDER D-800® from the supplier TOSHIKI.

Usual Additional Cosmetic Ingredients

The composition of the invention may furthermore comprise any usual cosmetic ingredient that may in particular be selected from anti-oxidants, fragrances, preservatives, neutralizing agents, surfactants, sunscreens, sweeteners, vitamins, moisturizers, emollients, hydrophilic or lipophilic active ingredients, free radical scavengers, sequestrating agents and mixtures thereof.

Clearly, the skilled person will take care to select any complementary ingredients and/or their quantity such that the advantageous properties of the composition of the invention are not, or are not substantially altered by the envisaged addition.

Application Devices

Examples will now be described of devices that, inter alia, can be used to implement a cosmetic treatment method comprising the steps consisting of:
  a) heating an application surface of a mass of solid product with the aid of an artificial heat source located externally of the product mass, especially an application surface of a stick of product, to heat it to a temperature higher than that of a portion of the product mass distanced from the application surface and which remains solid during application; and
  b) applying the thus heated application surface to a region to be treated, in particular the skin or lips.

The description of these devices is made with reference to the accompanying drawings in which:

FIG. 1 represents, in a diagrammatic manner, in elevation, an example of a packaging and application device produced in accordance with the invention;

FIG. 2 shows in isolation, in partial and diagrammatic longitudinal section, the cap of the device of FIG. 1;

FIG. 3 illustrates, diagrammatically and partially, heating up of the end of the stick by contact with a hot surface;

FIG. 4 represents in a diagrammatic and partial manner an example of an embodiment of the heating means;

FIGS. 5 to 7 illustrate details of embodiments of variations of the heating means;

FIG. 10 represents a stick and associated support means;

FIG. 12 is a longitudinal, partial and diagrammatic section of the device of FIG. 11;

FIG. 13 is a longitudinal, partial and diagrammatic section of a variation of an embodiment of the device;

FIG. 14 represents a variation in the packaging of the product; and

Figure 15:
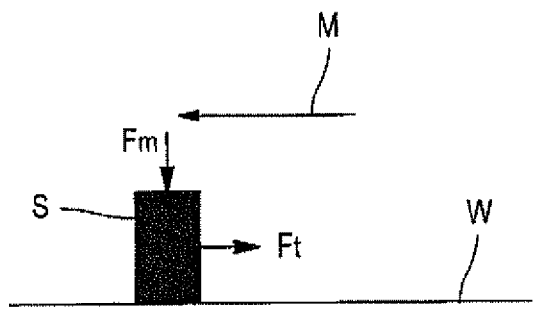

FIG. 15, described above, illustrates the measurement of the dynamic coefficient of friction.

The device 1 for packaging and application shown in FIG. 1 comprises a base portion 2 that supports a product mass of the invention in the form of a stick S of product, and a cap 3 that can be fixed on the base portion 2 to close the device 1 when not in use.

The base portion 2 may be of any known type allowing the stick S to be displaced as it is consumed.

The base portion 2 comprises, for example, two portions 5 and 6 that can turn with respect to each other, and a mechanism that can transform the relative rotation of the two portions 5 and 6 into an axial displacement along the longitudinal axis X of the stick S.

The stick S is, for example, carried in this mechanism by a cup 58 as shown in FIG. 10, comprising studs 59 engaged in two parts respectively belonging to portions 5 and 6, one of which has longitudinal rectilinear slots and the other of which has helical slots such that rotation of these two parts is accompanied by axial displacement of the cup and the stick S.

Examples of mechanisms that may be suitable are described in publications U.S. Pat. No. 6,340,258, U.S. Pat. No. 6,086,276, U.S. Pat. No. 6,371,673, U.S. Pat. No. 5,171,096 and U.S. Pat. No. 7,293,926, the contents of which are herewith incorporated by reference.

The cap 3 comprises a heating device 10 that can heat up the end 11 of the stick S prior to applying it to the keratinous materials, for example the skin or lips.

The heating device 10 may house a source of electricity, not shown, for example containing one or more storage batteries or cells, and a heating means comprising, for example, an electrical resistance supplied by the source of electricity.

Examples of heating means that may be suitable are disclosed in US 2007/0 286 665 A1, for example.

The heating means is disposed so as to raise the temperature of a heating surface 13 which, in the example shown in FIGS. 1 and 2, can come into contact with the stick S as shown in FIG. 3 in order to raise the temperature of the distal end 11 thereof.

The heating device 10 may comprise a switch 14 that enables the user to start or stop the heating device 10 as well as an operating indicator 15, for example a light that illuminates when the heating surface 13 is being heated.

The heating device 10 may optionally comprise any means for regulating the temperature of the heating surface 13, so that it does not exceed a predefined value.

When the heating surface is inaccessible to the user, a higher heating temperature that, however, is compatible with the product may be allowed. In contrast, when the heating surface 13 can be touched by the user, a temperature not exceeding 65° C. is preferred.

The heating device 10 may also if necessary incorporate a delay time which means that the end 11 of the stick S can only be heated up for a predefined period, in order to avoid premature wear of the source of electrical energy and/or to avoid heating the entire stick to an excessive temperature.

The heating device 10 may advantageously comprise any sensor that is suitable that can only start up the heating function in the case of effective contact of the heating surface with the end 11 of the stick S.

As an example, the heating device 10 may comprise a contact pressure sensor between the heating surface 13 and the stick S, and only allow the heating surface 13 to be heated when contact with the stick S is confirmed.

The heating surface 13 may, for example, be defined by a contact part 20, which is, for example, axially movable along the axis X relative to the body 22 of the heating device 10 against the resilience of an elastic return means 23 such as a spring, for example, housed inside the contact part 20, as illustrated in FIG. 4.

FIG. 4 represents a heating device comprising an electrical resistance 25 flush against the bottom of the contact part 20 so as to be as close as possible to the heating surface 13.

The contact part 20 may, for example, comprise a metal that is a good conductor of heat, with a small wall thickness, in order to have a low thermal inertia. In certain embodiments, the contact part 20 may, for example, comprise aluminum.

The heating surface 13 may have any shape adapted to the geometry of the end 11 of the stick, for example a bevel tip shape substantially complementary to the shape of the end 11 of the stick S, as illustrated in FIGS. 1 and 2, or another shape, for example a shape that is concave towards the stick S, in particular in the shape of a spherical hood as illustrated in FIG. 5, a conical or truncated cone shape as illustrated in FIG. 6 or a substantially planar shape perpendicular to the axis X, as illustrated in FIG. 7.

When the shape of the heating surface 13 is not a symmetrical body of revolution about the axis X, the device 1 may comprise means for rotational indexing of the base portion 2 and cap 3 so as to allow the cap 3 to be fixed on the base portion 2 only in a predefined angular orientation between the two, in which the heating surface 13 can be applied in a predefined manner, compatible with its geometry, against the stick S.

The stick S which is, for example, a stick of a lipstick, may have a section in the range 0.1 to 5 cm$^2$ or even in the range 0.15 to 1 cm$^2$, and the device 1 may be used by initially switching on the heating device 10 and waiting for the period necessary for the end 11 of the stick that defines the application surface to be heated to the desired temperature.

Coming up to temperature may, for example, be indicated by the light 15 which may, for example, change from a continuously illuminated state indicating that the device has been switched on to a flashing illumination or color change when the temperature is reached. Other methods for indicating the state of illumination may be used without departing from the scope of the invention.

Once the end of the stick has heated up, the base portion 2 can be separated from the cap 3 and the user can apply the product from the stick onto the lips or other keratinous materials. Softening of the product at the end 11 of the stick ensures comfortable application, good transfer onto the lips with a thick deposit that may be glossy on application.

As an example, the application may be carried out without using an applicator. In other words, only the composition, and more precisely the softened surface, is brought into direct contact with the region to be treated.

The body of the stick S is at ambient temperature or at a slightly higher but insufficient temperature to compromise the mechanical strength necessary to withstand the mechanical forces engendered by application. The difference in temperature between the application surface and the body of the stick, in particular at the end opposite to the application surface, is at least 20° C., for example, or even at least 30° C. when the stick is at its initial length, when used for the first time.

The device 1 may be used in a similar manner when making up the skin, whereupon the stick may have a larger section if appropriate.

Figure 8:
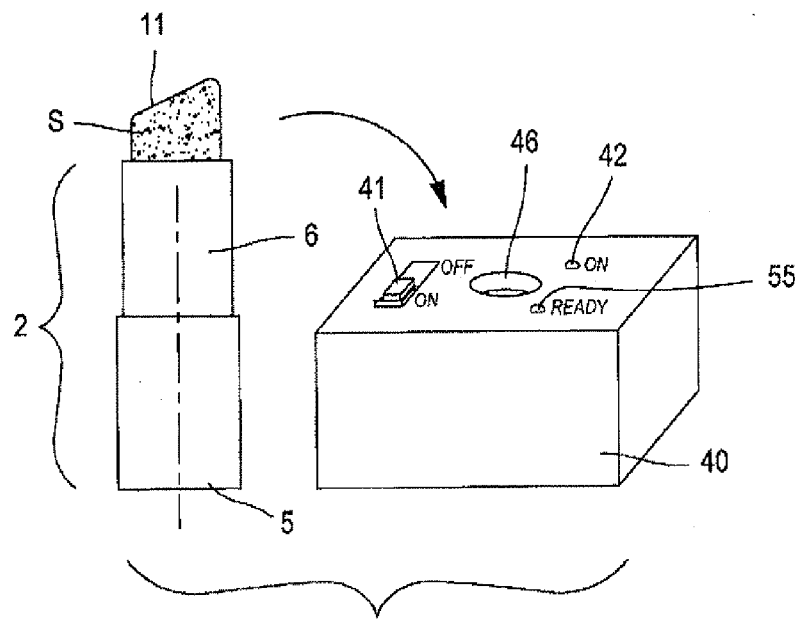
FIG. 8 represents in diagrammatic manner a variation of the embodiment of the packaging and application device.
Figure 9:
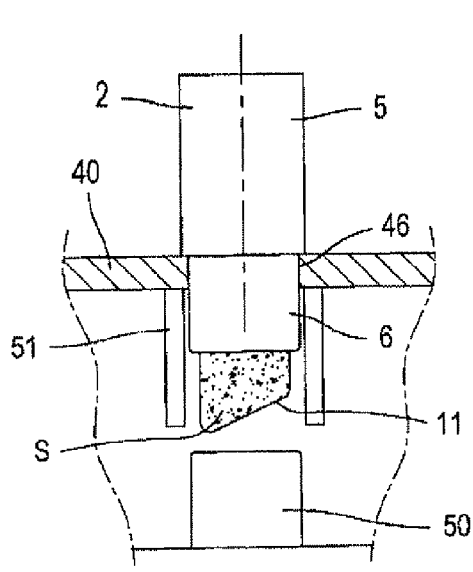
FIG. 9 is a diagrammatic and partial section of the device of FIG. 8, after placing in the corresponding recess of the housing.

The heating device does not have to be incorporated into a cap 3 of the packaging device, but be present in a housing 40 that is distinct from the device for packaging the stick S, as illustrated in FIGS. 8 and 9.

The housing 40 may house an electrical source and/or comprise a means for connection to an electrical source, for example the mains via a low voltage transformer.

The housing 40 may also comprise start means 41 such as a start/stop switch, as well as one or more lights 42 and 55 to indicate that it is connected to the power supply and/or when the operating temperature is reached.

In the example of FIGS. 8 and 9, the housing 40 comprises an opening 46 in which the base portion 2 may be introduced at least partially as illustrated in FIG. 9, in order to bring the end 11 of the stick close to a heating means 50 present in the housing 40.

The opening 46 has a section, for example, that is adapted to one of the parts of the base portion such that engaging that base portion in the housing brings the end 11 of the stick into a predefined position, in at least two directions in space, relative to the heating means.

The housing 40 may comprise any suitable sensor 51 that can detect positioning of the base portion 2 on the housing 40 and possibly the positioning of the stick relative to the heating means.

Heating the end of the stick S may take place by conduction, in contact with a hot surface, in the manner described above. In this case, the heating means comprises a heating surface that can be heated to an adequate temperature using any heating means, for example an electrical resistance.

The end of the stick may also be heated without contact, for example by IR radiation and/or convection, and/or by vibrations and/or radioelectrical radiation or any other source providing heat.

As mentioned above, the housing 40 may comprise any suitable sensor, especially optical, capable of evaluating the distance between the end 11 of the stick and the heating means 50 in order to ensure that it cannot be switched on until a predefined distance has been reached and/or to regulate the heating power as a function of the separation between the heating means and the end of the stick S.

In certain variations, the heating means 50 may be a system for heating by emitting infrared radiation towards the end 11 of the stick, for example by means of a halogen or incandescent lamp, or by blowing hot air towards the end 11.

In certain variations, the end 11 of the stick S may also be heated up by exposure to radioelectrical radiation, for example microwaves, focused at the end 11 of the stick S.

In yet more variations, the end 11 of the stick S may be heated up by ultrasound vibrations.

Figure 11:
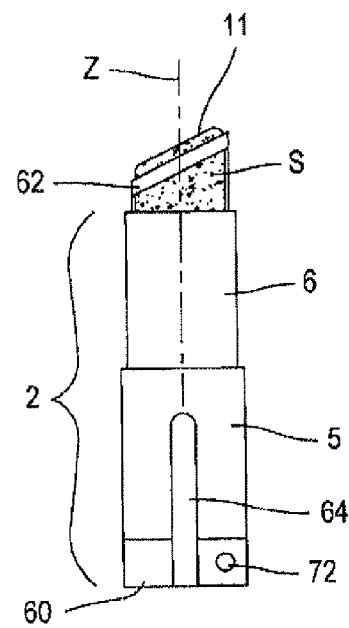
FIG. 11 represents a variation of the packaging and application device in elevation.

In the variation of FIGS. 11 and 12, the heating device 60 comprises a heating means 62 that is integral with the base portion 2 and which may comprise, as illustrated, an annular-shaped heating means 62, through which the stick S can pass. The heating means 62 has, for example, a section that is greater than or equal to that of the stick S.

The heating device 60 may, for example, comprise a control means 64 which the user can press to start the operation of the heating means 62. The heating means 62 may, for example, comprise a heating resistor that can heat up the end 11 of the stick S by conduction, convection and/or radiation (for example infrared, microwaves, etc.).

If necessary, the heating means 62 may also participate in application of the product associated with the stick S and to this end may have an upper face 70 of suitable shape, for example beveled.

In order to use the device in the example under consideration, the user can bring the end 11 of the stick to the heating means 62 and start heating by pressing the control means 64.

The heating device may comprise an indicator light 72 indicating the operation of the heating means 62 to the user.

The user may then interrupt heating when it can be visually ascertained that the end 11 of the stick has changed appearance following the rise in temperature, and for example has become glossy.

At that moment, the user can optionally then displace the end 11 a little further upwards in order to facilitate application of the product, without contact with the heating means 62. In a variation, the user can apply the product by bringing not only the stick S but also the heating means 62 into contact with the lips or the skin.

The outer surface of the heating means 62 may be tapered, as illustrated in FIG. 13, in order to reduce the contact surface between the treated region and the heating means 62.

FIG. 14 represents a variation in which the product mass S associated with the stick S is supported by a wand 200 suitable, for example, for single use.

The application surface 202 is heated up, for example, by being brought into contact with or close to a hot surface, for example by introducing it into a housing provided with a heating means such as the housing described above with reference to FIGS. 8 and 9.

EXAMPLES

In the examples below, the percentages by weight are indicated with respect to the total composition weight.

Example 1

Lipstick According to the Invention

|         |                                                           | Function   | % by weight |
|---------|-----------------------------------------------------------|------------|-------------|
| Phase A | Preservative                                              |            | 0.06        |
|         | Diisostearyl malate [1]                                   | glossy oil | 5.0         |
|         | Bis-diglyceryl polyacyladipate-2 [2]                      | pasty      | 11.15       |
|         | 1,3,5-trimethyl 1,1,3,5,5-pentaphenyl trisiloxane [3]     | glossy oil | 28.55       |
|         |                                                           | glossy oil | 16          |
|         | Hydrogenated castor oil/sebacic acid copolymer [4]        | fluid oil  | 5.05        |
|         | Phenyl trimethicone [5]                                   |            |             |
| Phase B | Iron oxides (and) iron oxides                             | pigment    | 4.30        |
|         | Blue 1 lake                                               |            | 1.3         |
|         | Titanium dioxide                                          |            | 1.79        |
|         | Red 28 lake                                               |            | 2.60        |
| Phase C | Microcrystalline wax [6]                                  | wax        | 3.10        |
|         | (hydroxystearyloxy)$C_{20-40}$ alkyl stearate [7]         | wax        | 3.10        |
| Phase D | Hydrogenated castor oil dimer dilinoleate [8]             |            | 5           |
|         | Hydrogenated castor oil isostearate [9]                   | pasty      | 5           |
|         | VP/EICOSENE COPOLYMER [10]                                |            | 5           |
| Phase E | HDI/trimethylol hexyllactone crosspolymer                 | filler     | 5           |
|         | TOTAL                                                     |            | 100         |

[1] Schercemol DISM sold by Lubrizol
[2] Softisan 649 sold by Sasol
[3] PH-1555 HRI sold by Dow Corning
[4] CRODABOND-CSA from the supplier CRODA
[5] Dow Corning 556 sold by Dow Corning
[6] Microwax HW sold by the supplier Paramelt
[7] Kester Wax K82H sold by KOSTER KEUNEN
[8] RISOCAST-DA-L sold by KOKYU ALCOHOL KOGYO
[9] Salacos HCISV-L sold by Nisshin Oillio
[10] Ganex V220F ® sold by the supplier ISP If necessary, the surface of the heating means 62 that can come into contact with the skin may be flocked or have a textured surface appearance facilitating application.

In the variation illustrated in FIG. 13, the stick S passes through a heating means 62 defining an opening 76 with a smaller section with respect to the section of the body of the stick.

In this example, softening of the stick S in contact with the heating means 62 may then be accompanied by deformation of the stick through the heating means 62. This can increase the accuracy of application of the product and prevent the stick S from being advanced so far with respect to the heating means 62 that sufficient softening is not achieved.

The ingredients of phase A were added to a pan. They were agitated with a Rayneri, heating gently to 50° C. The pigments of phase B were ground into a portion of phase A. The ground material, the other portion of phase A, the waxes of phase C and the pasty fats of phase D were added to a double-walled pan. They were all heated to 98-100° C., agitating with a Rayneri until the waxes were melted. Finally, the filler (phase E) was added to the mixture which was poured into a mold to produce 12.7 mm diameter lipsticks. The molds were then placed at −20° C. for half an hour and the sticks were unmolded, and mounted in the lipstick mechanisms as illustrated in FIG. 8, for example.

The lipstick had a dynamic coefficient of friction of 1.05 at 25° C. and a hardness at 20° C. equal to 146 $Nm^{-1}$.

Example 2

Lipstick According to the Invention

|  |  | Function | % by weight |
|---|---|---|---|
| Phase A | Hydrogenated castor oil isostearate [1] | pasty | 15.96 |
| Phase B | Polybutylene [2] | Glossy oil | 10 |
|  | Diisostearyl malate [3] |  | 12.5 |
|  | Dimer dilinoleyl dimer dilinoleate [4] |  | 12.5 |
| Phase C | Bis-diglyceryl polyacyladipate-2 [5] | pasty | 17.86 |
|  | Bis-behenyl/isostearyl/phytosteryl dimer dilinoleyl [6] | pasty | 17.14 |
|  | Polyethylene [7] | wax | 4.79 |
|  | Poly $C_{10-30}$ alkyl acrylate [8] | polymer semicrystalline | 5.00 |
| Phase D | Yellow 6 lake | pigment | 1.29 |
|  | Blue 1 lake |  | 0.08 |
|  | Red 7 |  | 0.30 |
|  | Titanium dioxide [9] |  | 1.37 |
|  | Iron oxides |  | 0.16 |
| Phase E | Mica (and) titanium dioxide (and) iron oxides [10] | nacre | 1.00 |
|  | Fragrance |  | 0.05 |
|  | TOTAL |  | 100 |

[1] Salacos HCISV-L sold by Nisshin Oillio
[2] Indolol H 100 sold by INEOS
[3] Schercemol DISM sold by Lubrizol
[4] Lusplan DD-DA7 sold by Nippon Fine Chemical
[5] Softisan 649 sold by Sasol
[6] Plandool-G sold by Nippon Fine Chemical
[7] Performalene 500-L sold by New Phase Technologies
[8] Intelimer IPA 13-1 sold by Air Products and chemicals
[9] Tipaque PF-671 sold by Ishihara Sangyo
[10] Cloisonne Sparkle Gold 222 J sold by BASF The pigments of phase D were ground in phase A.

The ground material, phase B and the ingredients of phase C were added to a double-walled pan. They were all heated to 98-100° C., agitating with a Rayneri until the ingredients had completely melted.

Finally, the nacre (phase E) was added to the mixture, which was poured into a mold to produce 11.06 mm diameter lipsticks. The molds were then placed at −20° C. for half an hour and the sticks were unmolded.

The hardness of the stick at 20° C. was 156 $Nm^{-1}$.

At ambient temperature, the composition obtained deposited very little and had a great deal of grab.

In order to illustrate the invention, the beveling of the composition was brought into contact with a hot source at 60° C. for 10 seconds then applied to the lips: the application was more agreeable compared with application carried out at ambient temperature as disclosed above, the deposit on the lips was glossy with good staying power and gloss and without migration.

Clearly, the invention is not limited to the examples that have just been illustrated.

In the case in which the stick is displaced relative to a heating means, displacement of the stick may be carried out by means of a mechanism comprising at least two portions that are movable in rotation or by a mechanism displacing the stick by increments. Examples of such incrementally displacing mechanisms are, for example, encountered in hot melt glue guns; an example thereof is given in US 2003/0 150 875 or US 2006/0 191 957.

In a variation, the heating resistor is integrated into the base portion or into the cap closure thereof and it is supplied with a source of electricity that is located on a housing with which the base portion or the cap must be brought into engagement to be connected electrically. This means that incorporating one or more storage batteries or cells into the base portion or the cap can be avoided.

In a variation, the base portion or the cap comprises at least one storage battery and this is recharged by placing the base portion or the cap on a charging station.

The end of the stick may also be heated by mechanical action by the user, for example by causing a wheel mounted rotatably on the cap to rotate and which is engaged with a sliding contact, such that rotation of the wheel causes the temperature of the sliding contact to rise, this temperature rise being transmitted via a contact piece to the end of the stick.

The invention is not limited to a lipstick or to a product for making up or care of the skin or the lips.

The product may be present on a palette when it is being heated up.

The expression "comprising a" should be construed as being synonymous with "comprising at least one" unless otherwise specified.

The invention claimed is:

1. A method for applying lipstick to the lips, comprising:
   bringing an outer surface of a piece of lipstick into contact with or into the vicinity of a heating device so as to heat said piece of lipstick in a localized manner; and
   then applying the heated lipstick;
   said lipstick comprising a quantity of 10% to 80% by weight of a glossy oil with respect to the total lipstick weight, said glossy oil being a hydrocarbon or silicone oil with a molecular mass of 500 to approximately 10,000 g/mol or more;
   wherein the heating device comprises batteries as source of electrical energy.

2. The method as claimed in claim 1, wherein the molar mass is between 550 to 7500 g/mol.

3. The method as claimed in claim 1, wherein the lipstick comprises a hydrocarbon glossy oil selected from lipophilic polymers selected from polybutylenes, hydrogenated polyisobutylenes, polydecenes and hydrogenated polydecenes, vinylpyrrolidone copolymers; esters selected from esters of linear fatty acids with a total carbon number ranging from 35 to 70, polyglyceryl-2 triisostearate, triisocetyl citrate, diisostearyl malate, tridecyl trimellitate, esters of branched $C_{24}$-$C_{28}$ fatty alcohols or fatty acids, dimeric diol and dimeric diacid esters with general formula:

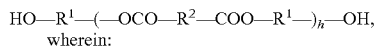

wherein:

$R^1$ represents a dimeric diol residue obtained by hydrogenation of dilinoleic diacid;

$R^2$ represents a hydrogenated dilinoleic diacid residue; and h represents a whole number from 1 to 9;

sesame oil ligoester, wherein the monomers are represented by triglyceride (A) and diacid (B) formulae:

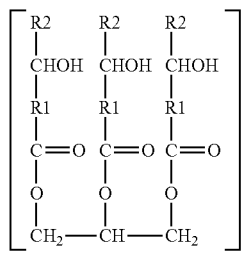 (A)

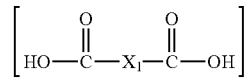 (B)

wherein $R_1$ represents a saturated or unsaturated, linear or branched alkylene group containing 1 to 18 carbon atoms, and $R_2$ represents a saturated or unsaturated, linear or branched alkyl group containing 1 to 12 carbon atoms.

4. The method according to claim 1, wherein the glossy oil is present in the lipstick in an amount from 30% to 60% by weight with respect to the total lipstick weight.

5. The method as claimed in claim 1, wherein the lipstick further comprises a fluid oil with molar mass of from 100 to 390 g/mol.

6. The method as claimed in claim 1, wherein the lipstick further comprises a solid fat that is a wax or a pasty compound.

7. The method as claimed in claim 1, wherein the lipstick further comprises at least one colorizing agent.

8. The method as claimed in claim 7, wherein the colorizing agent is a hydrosoluble dye, a liposoluble due, a pigment, a nacre, or a mixture thereof.

* * * * *

UNITED STATES PATENT AND TRADEMARK OFFICE
CERTIFICATE OF CORRECTION

PATENT NO. : 8,945,524 B2
APPLICATION NO. : 13/054681
DATED : February 3, 2015
INVENTOR(S) : Philippe Ilekti et al.

It is certified that error appears in the above-identified patent and that said Letters Patent is hereby corrected as shown below:

In the Claims

Column 41, line 10, "sesame oil ligoester, wherein the monomers are represented"

should read

--sesame oil, oligoester, wherein the monomers are represented--.

Signed and Sealed this
Twenty-fifth Day of August, 2015

Michelle K. Lee
*Director of the United States Patent and Trademark Office*